United States Patent
Cao et al.

(10) Patent No.: US 9,993,291 B2
(45) Date of Patent: Jun. 12, 2018

(54) RADIO FREQUENCY ABLATION METHOD, SYSTEM AND RADIO FREQUENCY ABLATION DEVICE THEREOF

(71) Applicant: SHANGHAI GOLDEN LEAF MED TEC CO., LTD, Shanghai (CN)

(72) Inventors: Hongguang Cao, Shanghai (CN); Yonghua Dong, Shanghai (CN); Jiuling Guo, Shanghai (CN)

(73) Assignee: SHANGHAI GOLDEN LEAF MED TEC CO., LTD, Shanghai (CN)

( * ) Notice: Subject to any disclaimer, the term of this patent is extended or adjusted under 35 U.S.C. 154(b) by 251 days.

(21) Appl. No.: 14/766,637

(22) PCT Filed: Feb. 7, 2014

(86) PCT No.: PCT/CN2014/000143
§ 371 (c)(1),
(2) Date: Aug. 7, 2015

(87) PCT Pub. No.: WO2014/121664
PCT Pub. Date: Aug. 14, 2014

(65) Prior Publication Data
US 2015/0374435 A1    Dec. 31, 2015

(30) Foreign Application Priority Data

Feb. 7, 2013   (CN) .......................... 2013 1 0049148
Feb. 7, 2013   (CN) ...................... 2013 2 0071750 U
(Continued)

(51) Int. Cl.
*A61B 18/14*   (2006.01)
*A61B 5/00*   (2006.01)
(Continued)

(52) U.S. Cl.
CPC ........ *A61B 18/1492* (2013.01); *A61B 5/0073* (2013.01); *A61B 5/01* (2013.01);
(Continued)

(58) Field of Classification Search
None
See application file for complete search history.

(56) References Cited

U.S. PATENT DOCUMENTS

2008/0015570 A1 *   1/2008   Ormsby ............. A61B 18/1492
                                                          606/41
2012/0116253 A1 *   5/2012   Wallace ............... A61B 5/6885
                                                          600/587
(Continued)

FOREIGN PATENT DOCUMENTS

CN    1361676 A    7/2002
CN    2543497 Y    4/2003
(Continued)

OTHER PUBLICATIONS

International Search Report for PCT/CN2014/000143 dated May 13, 2015.

*Primary Examiner* — Ankit D Tejani
(74) *Attorney, Agent, or Firm* — Hauptman Ham, LLP

(57) ABSTRACT

A radio frequency ablation device, comprising a radio frequency ablation tube (10), a control handle (20) and a temperature-controlling radio frequency instrument (35). The middle section of the radio frequency ablation tube (10) carries a strip-shaped connecting electrode; a radio frequency electrode (12) is formed at the distal end of the radio frequency ablation tube (10) and connected to the control handle (20) via the strip-shaped connecting electrode. The control handle (20) comprises a control guiding control a tube electrode control handle (23) and a tube electrode auxiliary control handle (24) An integrated interface (50) is disposed at the rear of the control handle (20), and the
(Continued)

temperature-controlling radio frequency instrument (35) is connected to the integrated interface (50) via an integrated cable (34). And a radio frequency electrode (12) a radio frequency ablation tube (10) and a guide tube (16) are also provided.

9 Claims, 32 Drawing Sheets

(30) Foreign Application Priority Data

| Sep. 30, 2013 | (CN) | 2013 1 0463990 |
|---|---|---|
| Oct. 29, 2013 | (CN) | 2013 1 0522732 |
| Oct. 30, 2013 | (CN) | 2013 1 0530007 |
| Jan. 24, 2014 | (CN) | 2014 1 0035836 |
| Jan. 24, 2014 | (CN) | 2014 1 0035873 |

(51) Int. Cl.
| | | |
|---|---|---|
| *A61B 5/01* | (2006.01) | |
| *A61B 5/053* | (2006.01) | |
| *A61B 8/12* | (2006.01) | |
| *A61B 18/12* | (2006.01) | |
| *A61B 18/00* | (2006.01) | |

(52) U.S. Cl.
CPC .............. *A61B 5/053* (2013.01); *A61B 8/12* (2013.01); *A61B 18/1206* (2013.01); *A61B 2018/0072* (2013.01); *A61B 2018/00178* (2013.01); *A61B 2018/00267* (2013.01); *A61B 2018/00273* (2013.01); *A61B 2018/00404* (2013.01); *A61B 2018/00434* (2013.01); *A61B 2018/00577* (2013.01); *A61B 2018/00648* (2013.01); *A61B 2018/00702* (2013.01); *A61B 2018/00714* (2013.01); *A61B 2018/00761* (2013.01); *A61B 2018/00791* (2013.01); *A61B 2018/00827* (2013.01); *A61B 2018/00875* (2013.01); *A61B 2018/00898* (2013.01); *A61B 2018/00928* (2013.01); *A61B 2018/00958* (2013.01); *A61B 2018/00988* (2013.01); *A61B 2218/007* (2013.01)

(56) References Cited

U.S. PATENT DOCUMENTS

| 2012/0265186 A1* | 10/2012 | Burger | A61B 17/8811 606/21 |
|---|---|---|---|
| 2013/0006228 A1* | 1/2013 | Johnson | A61B 18/1477 606/14 |

FOREIGN PATENT DOCUMENTS

| CN | 2557081 | Y | 6/2003 |
|---|---|---|---|
| CN | 1596085 | A | 3/2005 |
| CN | 2855350 | Y | 1/2007 |
| CN | 2894642 | Y | 5/2007 |
| CN | 200942123 | Y | 9/2007 |
| CN | 200960161 | Y | 10/2007 |
| CN | 101190146 | A | 6/2008 |
| CN | 201194837 | Y | 2/2009 |
| CN | 102014779 | A | 4/2011 |
| CN | 102271750 | A | 12/2011 |
| CN | 102274021 | A | 12/2011 |
| CN | 102462532 | A | 5/2012 |
| CN | 102551672 | A | 7/2012 |
| CN | 102596081 | A | 7/2012 |
| CN | 202365923 | U | 8/2012 |
| CN | 102688090 | A | 9/2012 |
| CN | 102781338 | A | 11/2012 |
| CN | 202821623 | U | 3/2013 |
| CN | 202933013 | U | 5/2013 |
| CN | 103271765 | A | 9/2013 |
| CN | 103505798 | A | 1/2014 |
| CN | 103519888 | A | 1/2014 |
| CN | 103536356 | A | 1/2014 |
| CN | 203524766 | U | 4/2014 |
| EP | 0904739 | A2 | 3/1999 |
| WO | 9324050 | A1 | 12/1993 |
| WO | 0066021 | A1 | 11/2000 |
| WO | 2008082988 | A1 | 7/2008 |
| WO | 2012086492 | A1 | 6/2012 |

* cited by examiner

RADIO FREQUENCY ABLATION METHOD, SYSTEM AND RADIO FREQUENCY ABLATION DEVICE THEREOF

CROSS REFERENCE TO RELATED APPLICATION

This application claims the priority of International Application No. PCT/CN2014/000143, filed on Feb. 7, 2014, which claims priorities to Chinese Application No. 201310049148.X, filed on Feb. 7, 2013, Chinese Application No. 201320071750.9, filed on Feb. 7, 2013, Chinese Application No. 201310463990.8, filed on Sep. 30, 2013, Chinese Application No. 201310522732.2, filed on Oct. 29, 2013, Chinese Application No. 201310530007.X, filed on Oct. 30, 2013, Chinese Application No. 201410035873.6, filed on Jan. 24, 2014 and Chinese Application No. 201410035836.5, filed on Jan. 24, 2014. The entire disclosures of each of the above applications are incorporated herein by reference.

BACKGROUND

Technical Field

The present invention relates to a radio frequency ablation method used for nerve ablation, and also relates to a radio frequency ablation system. The present invention further relates to a radio frequency ablation device for implementing the foregoing method.

Related Art

During occurrence, evolution, and development of many diseases, an abnormity in an autonomic nerve is a key factor that has an important effect. For example, excessive enhancement of the activity of a renal sympathetic nerve has an important effect in many diseases, such as resistant hypertension, chronic cardiac insufficiency, renal insufficiency, disturbance of carbohydrate metabolism, and polycystic ovary syndrome. For another example, the effect of overexcitation of a pneumogastric nerve on a gastrointestinal ulcer has also attracted long-term attention and research in the field of medicine, and severing a pneumogastric nerve can reduce the secretion of gastric acid. For another example, although the pathogenesis of asthma is still not completely clear today, there is enough evidence to prove that autonomic neurological disorder is an important factor in the occurrence and development of asthma.

As early as in the middle of the last century, scholars attempted to use surgical resection to treat resistant hypertension. Although such resection was initially abandoned because of the occurrence of serious complications, these clinical experiments had also proven the potential therapeutic value of renal sympathetic nerve block.

In recent years, percutaneous renal sympathetic nerve ablation using a minimally invasive technology starts to be applied clinically and achieves a desirable effect. Besides, a radio frequency ablation technology has found wide application in treatment of multiple types of focal tissue such as heart, cancerous tumor and even skin. By using the characteristic that treatment points are concentrated due to rapid attenuation of a temperature field near a conductor when radio frequency energy acts on human tissue, minimally invasive treatment is performed on focuses by using a small catheter probe.

SUMMARY

A major technical problem to be solved in the present invention is to provide a radio frequency ablation method used for nerve ablation.

Another technical problem to be solved in the present invention is to provide a radio frequency ablation system used for implementing the foregoing radio frequency ablation method.

Still another technical problem to be solved in the present invention is to provide a radio frequency ablation device used for implementing the foregoing radio frequency ablation method.

To achieve the foregoing objectives of the present invention, the present invention adopts the following technical solutions:

A radio frequency ablation method used for nerve ablation includes the following steps:

(1) collecting and storing basic information of a patient;

(2) after the distal end of a radio frequency ablation tube reaches a target lumen, locating target tissue by measuring impedance, and adhering a radio frequency electrode to a vascular wall around the target tissue;

(3) generating radio frequency ablation guiding parameters (guiding parameters for short) according to the basic information of the patient from a database; and selecting a group of guiding parameters to start a radio frequency ablation process;

(4) monitoring the impedance changed of the target tissue in the radio frequency ablation process, and adjusting radio frequency parameters accordingly; and (5) determining whether the impedance value of the target tissue is within a preset impedance threshold range; if the result is yes, stopping radio frequency and storing the radio frequency parameters; and if the result is no, repeating step (4) until the impedance value of the target tissue is within the preset impedance threshold range.

As a preferred embodiment of the foregoing radio frequency ablation method, in step (3), the guiding parameters include: radio frequency output power, radio frequency loading duration time, a set temperature, and an impedance threshold.

As another preferred embodiment of the foregoing radio frequency ablation method, in step (4), besides monitoring the impedance changed of the target tissue, a step of monitoring a tissue temperature changed in the radio frequency ablation process is further included, and it is determined whether the temperature value exceeds a set threshold; if the result is no, radio frequency is continued; and if the result is yes, radio frequency is stopped, an automatic alarm is raised, and the radio frequency parameters are recorded.

A radio frequency ablation system includes a central processing and control module; a radio frequency releasing module, a impedance measuring module, and a temperature monitoring module that are separately connected to the central processing and control module; and an alarm and automatic storage module connected to the central processing and control module, where the central processing and control module is used to generate guiding parameters and is also used to control the radio frequency releasing module according to monitoring results of the impedance measuring module and the temperature monitoring module;

the impedance measuring module is used to measure impedance of target tissue, to provide a basis for locating the target tissue and determining the extent of damage by radio frequency;

the temperature monitoring module is used to perform real-time monitoring on temperature around the target tissue, to prevent a target lumen from being excessively damaged; and the alarm and automatic storage module is used to comprehensively analyze signals from the impedance measuring module and the temperature monitoring module, and raise an alarm in time for a situation in which any signal exceeds a preset safety threshold, and is used to arrange and store used parameters and collected information in an ablation process.

As a preferred embodiment of the foregoing radio frequency ablation system, an intra-cavity optical tomography imaging module and an intra-cavity ultrasound imaging module that are separately connected to the central processing and control module are further included, where the intra-cavity optical tomography imaging module is used to perform real-time dynamic imaging monitoring on a vascular wall around the target tissue; and the intra-cavity ultrasound imaging module is used to perform ultrasound imaging monitoring on the vascular wall around the target tissue.

A radio frequency ablation device includes a radio frequency ablation tube, a control handle, and a temperature-controlling radio frequency instrument, where the middle section of the radio frequency ablation tube carries a strip-shaped connecting electrode, a radio frequency electrode is formed at the distal end of the radio frequency ablation tube, and the radio frequency electrode is connected to the control handle via the strip-shaped connecting electrode;

the control handle includes a tube guiding control handle for controlling the degree of curvature of the distal end of the radio frequency ablation tube, and a tube electrode control handle and a tube electrode auxiliary control handle for controlling the degree of opening of the radio frequency electrode;

the temperature-controlling radio frequency instrument includes a central processing and control module; a radio frequency releasing module, a impedance measuring module, a temperature monitoring module, and an alarm and automatic storage module that are separately connected to the central processing and control module; and an integrated interface is disposed at the rear of the control handle, and the temperature-controlling radio frequency instrument is connected, via an integrated cable, to the integrated interface disposed on the control handle.

As a preferred embodiment of the foregoing radio frequency ablation device, a wall-penetrating section is disposed at a wall-adherence radio frequency position of the radio frequency electrode.

As a preferred embodiment of the foregoing radio frequency ablation device, a guide tube disposed outside the radio frequency ablation tube is included, where the guide tube has an anti-electromagnetic interference function, where the guide tube includes a cylindrical hollow tube body, where a port is disposed at the front of the tube body, a rear interface is disposed at the rear of the tube body, the tube body and the rear interface include a shielding mesh woven by a conductive material, the conductive material is woven crosswise along a tube wall of the tube body to form a closed annular shielding mesh, and the shielding mesh is led out at the rear interface to form a joint, where the joint is grounded.

As a preferred embodiment of the foregoing radio frequency ablation device, the radio frequency electrode has both a temperature measuring function and an impedance measuring function;

the radio frequency electrode includes a radio frequency releasing point, where the radio frequency releasing point is also used as an impedance measuring point; and a second material is connected to the radio frequency electrode for forming a temperature measuring thermocouple, where the second material refers to a material different from the material used for forming the radio frequency electrode.

As a preferred embodiment of the foregoing radio frequency ablation device, multiple grooves are formed on the surface of the radio frequency ablation tube; and the radio frequency ablation tube includes a support tube configured at the central part of the ablation tube, and multiple wires configured on the outer surface of the support tube, where the multiple wires are configured around the circumferential direction of the support tube, and each of the wires extends along the length direction of the support tube; and a sealing layer used for cladding the wire is configured outside each of the wires, and each neighboring sealing layers form a groove on the outer surface of the support tube.

As a preferred embodiment of the foregoing radio frequency ablation device, the tube body of the radio frequency ablation tube is a cable-integrated tube body manufactured by using a cable manufacturing process, one end of the tube body is used for being connected to a control handle, and the other end of the tube body is used for manufacturing an electrode section.

In the radio frequency ablation method provided by the present invention, by providing guiding parameters before an operation, blindness in a radio frequency operation is eliminated, and by using multiple monitoring methods in radio frequency ablation process, ablation to a target nerve can be monitored dynamically in real time, the degree of nerve ablation can be guide controlled and handed, curative effect and treatment precision are improved, and complications are prevented.

BRIEF DESCRIPTION OF THE DRAWINGS

FIG. 7a is an enlarged view of the front section of a radio frequency ablation tube in the radio frequency ablation tube shown in FIG. 6a;

FIG. 11b is a schematic diagram of a wall-penetrating state coronal surface in the petal-shaped cavity-passing and wall-penetrating radio frequency ablation tube shown in FIG. 11a;

FIG. 12b is a schematic diagram of a wall-penetrating state of the puncture needle-shaped cavity-passing and wall-penetrating radio frequency ablation tube shown in FIG. 12a;

FIG. 17b is a schematic diagram of an open state of the puncture needle-shaped radio frequency electrode shown in FIG. 17a;

DETAILED DESCRIPTION

Technical content of the present invention is described in detail below with reference to the accompanying drawings and specific embodiments.

To eliminate blindness of radio frequency ablation in the prior art, the present invention provides a radio frequency ablation method using guiding parameters and multiple monitoring methods, a radio frequency ablation system and a radio frequency ablation device that are used for implementing the radio frequency ablation method.

Figure 1:
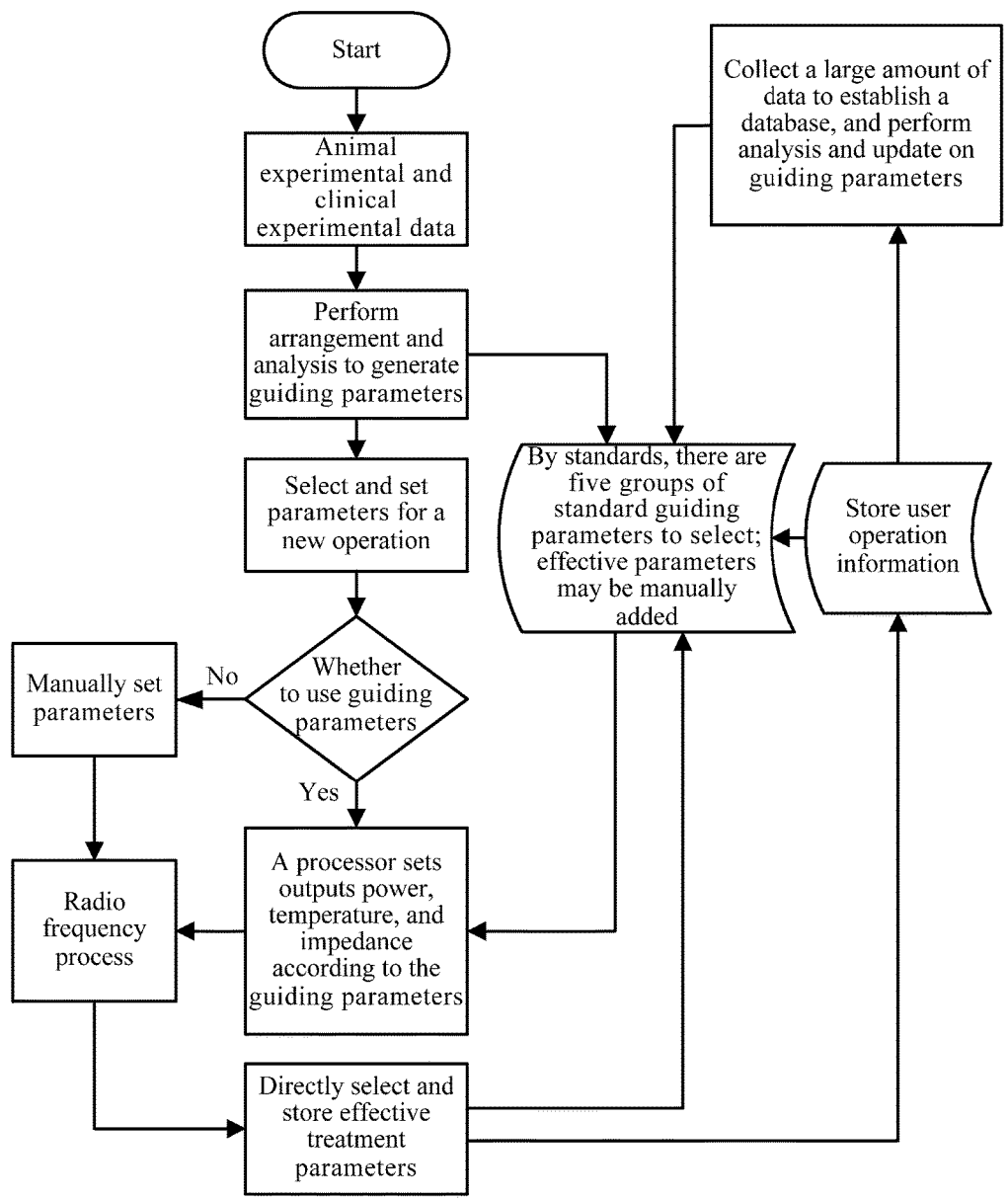
FIG. 1 is a processing flowchart of updating radio frequency ablation guiding parameters.

As shown in FIG. 1, guiding parameters used in the radio frequency ablation method are initially from existing clinical experimental and animal experimental data, and constant update and adjustment may be performed via subsequent clinical experiments. Before a radio frequency operation, the radio frequency ablation system may automatically generate one or more groups of guiding parameters from a database according to basic information of a patient (for example: gender, age, medical history, indexes of physiological and biochemical tests, and a living area, and so on), for selection and use by an operation executor. Each group of guiding parameters from the database is experimental data with a high success rate for a patient of the same kind, and therefore has high guiding significance. The guiding parameters include radio frequency output power, radio frequency loading duration time, a radio frequency load interception interval time, a repetition count, and a set temperature, and may further include other related information such as an impedance setting range and a temperature threshold range. Each parameter in the guiding parameters may be a determined value, or may be a value range with reference value. Meanings of these guiding parameters include content such as electrode impedance of different areas, an electrophysiological activity, a preset temperature, output power and time, a power time product, and a comparison difference between the foregoing parameters before and after treatment is implemented. The operation executor may select a value from these guiding parameters for use, and adjust the value in an operation process according to the extent of nerve damage. After the radio frequency operation is finished, the system may automatically store operation data into the database to update the database, for generating more accurate guiding parameters subsequently. The guiding parameters are also recorded by a related device, and become evidence traceable for a long time.

In the radio frequency ablation method, to accurately determine a target tissue ablation area, and determine the degree of nerve ablation, volume impedance measuring is performed on tissue separately before an operation, during an operation, and after an operation. Because nerve tissue has a low impedance characteristic, the distribution condition of the nerve tissue may be detected via a electrode, and because tissue degeneration and dehydration of radio frequency ablation may increase impedance of the target tissue, the ablation degree of the nerve tissue may be indirectly reflected by comparing impedance changes before and after nerve ablation. Therefore, in the radio frequency ablation method provided by the present invention, the target tissue is located before an operation by measuring impedance of tissue, to guide accurate selection of an ablation electrode position; and during an operation, the damage ablation degrees of the target tissue and a vessel are determined by monitoring a change of impedance, so as to determine accurate time to perform or stop ablation.

To ensure a safe ablation operation, in the radio frequency ablation method and the radio frequency ablation system provided by the present invention, a real-time monitoring step and a device to be used are further added. For example, a impedance measuring module is added to perform real-time monitoring on impedance in a radio frequency process, and a temperature monitoring module is added to perform real-time monitoring on temperature in a radio frequency process; for another example, an intra-cavity optical tomography imaging module and an intra-cavity ultrasound imaging module are added to perform real-time imaging monitoring on a vascular wall around the target tissue; and when it is monitored that the temperature of the vascular wall around the target tissue exceeds a set threshold, radio frequency is stopped and an automatic alarm is raised, which can prevent the vascular wall around the target tissue from being excessively damaged.

The radio frequency ablation method and the radio frequency ablation system thereof provided by the present invention are summarized above, and are described in detail below with reference to the accompanying drawings.

Figure 2:
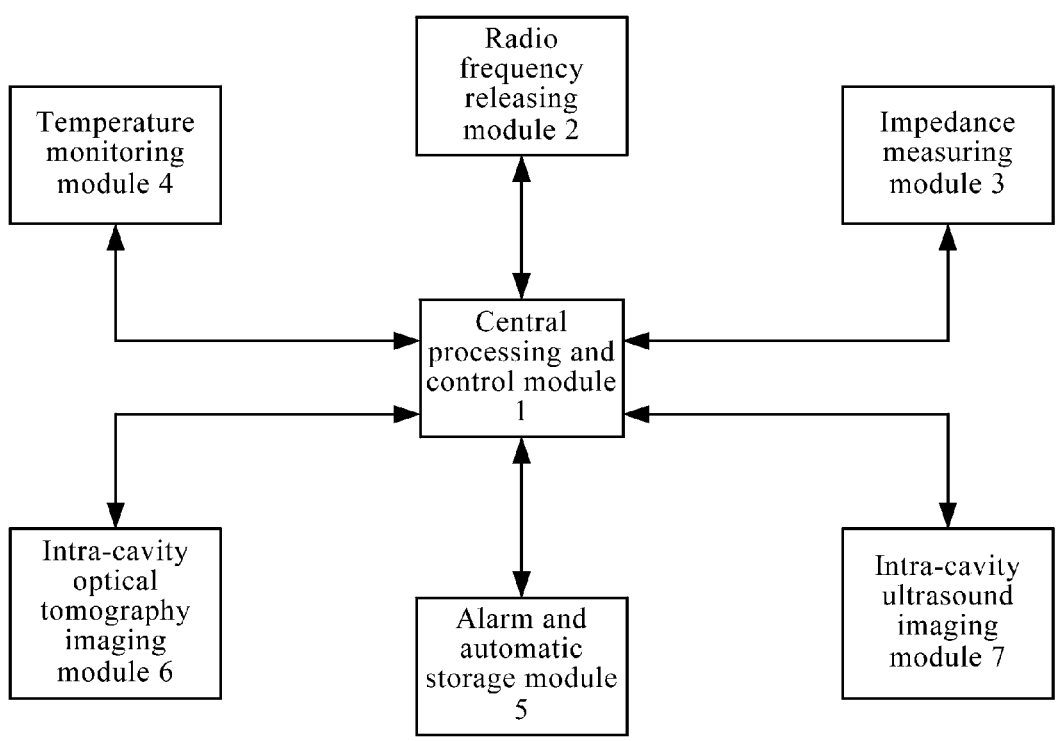
FIG. 2 is a block diagram of a data processing function of a radio frequency ablation system.

As shown in FIG. 2, a radio frequency ablation system provided by the present invention includes a central processing and control module 1, a radio frequency releasing module 2; a impedance measuring module 3, and a temperature monitoring module 4 that are separately connected to the central processing and control module 1; and an alarm and automatic storage module 5 connected to the central processing and control module 1, and in addition, further includes an intra-cavity optical tomography imaging module 6 and an intra-cavity ultrasound imaging module 7 that are separately connected to the central processing and control module 1.

The central processing and control module 1 is the core of the entire system, and is used to collect data of each module connected to the central processing and control module 1 and perform analysis. First, the central processing and control module 1 generates guiding parameters according to basic information of a patient from a database; next, locates target tissue according to a impedance measuring result; and finally, determines the degree of nerve ablation of the target tissue according to monitoring results of the monitoring modules (including the impedance measuring module 3, the temperature monitoring module 4, the intra-cavity optical tomography imaging module 6, and the intra-cavity ultrasound imaging module 7), and controls a radio frequency releasing process of the radio frequency releasing module 2.

The radio frequency releasing module 2 performs radio frequency releasing under the control of the central processing and control module 1, and performs ablation on the target tissue of a nerve.

The impedance measuring module 3 is used to measure impedance of the target tissue, to provide a basis for locating the target tissue and determining the extent of damage of the radio frequency; the temperature monitoring module 4 is used to perform real-time monitoring on temperature around the target tissue, to prevent a target lumen from being excessively damaged; the intra-cavity optical tomography imaging module 6 is used to perform real-time dynamic optics imaging monitoring on a vascular wall around the target tissue; and the intra-cavity ultrasound imaging module 7 is used to perform ultrasound imaging monitoring on the vascular wall around the target tissue. The alarm and automatic storage module 5 is used to comprehensively analyze signals from each monitoring module (the impedance measuring module 3, the temperature monitoring module 4, the intra-cavity optical tomography imaging module 6, and the intra-cavity ultrasound imaging module 7), and raise an alarm in time for a situation in which any signal exceeds a preset safety threshold, and is used to automatically arrange and store used parameters and collected data information in an ablation process.

Figure 3:
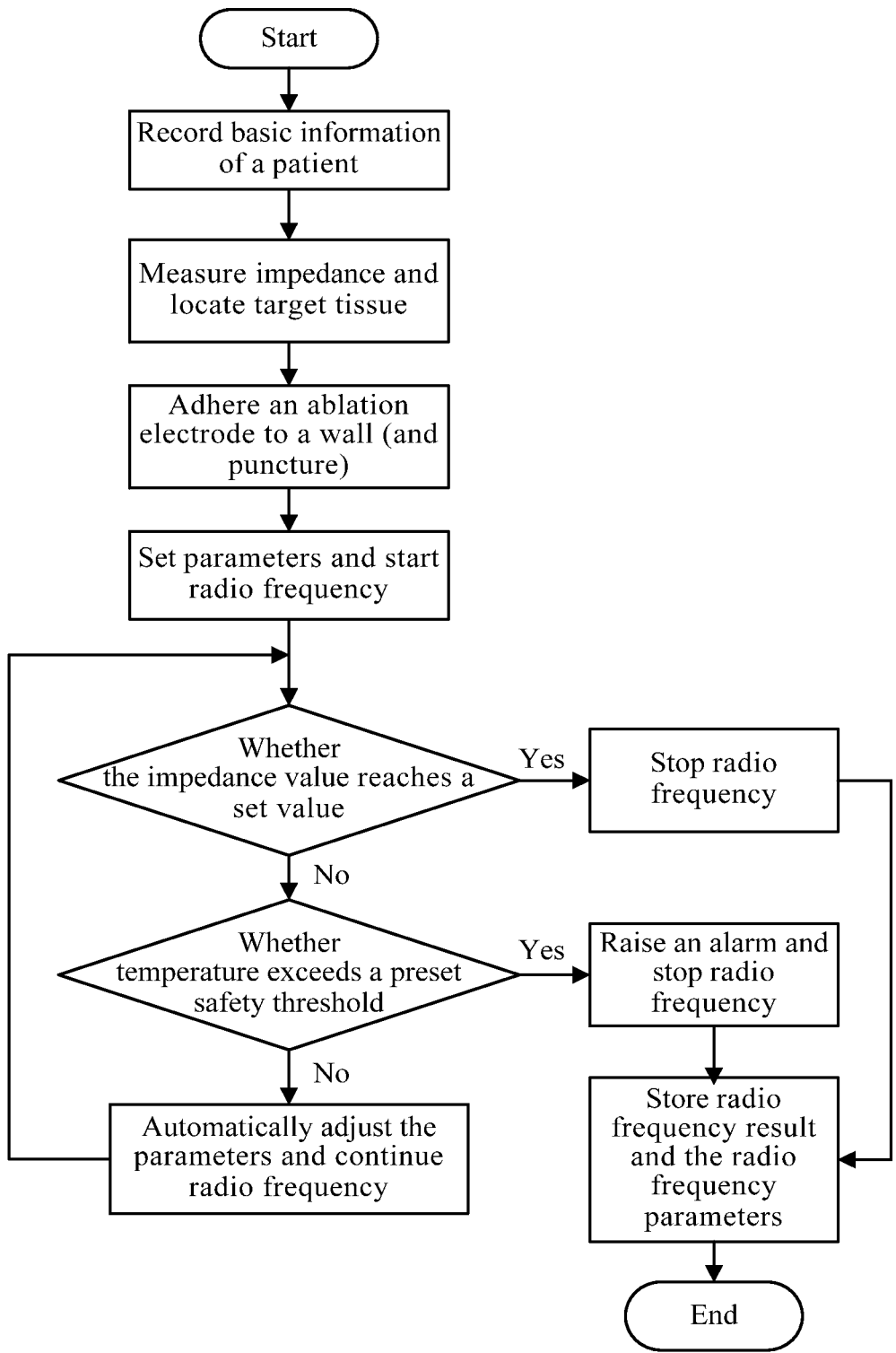
FIG. 3 is a flowchart of data processing in a radio frequency operation process.

The radio frequency ablation method provided by the present invention is described below with reference to a flowchart of data processing shown in FIG. 3. Specifically, the following steps are included:

(1) Before an operation, record and store basic information of a patient, collect data including name, age, gender, race, a living area, blood pressure, and cardiac rhythm of the patient, perform comprehensive analysis on whether the patient has diseases in other organs such as heart and lung, and provide a condition for data analysis and database establishment.

(2) Use a conventional interventional technology to insert a radio frequency ablation tube selectively into a target lumen of the patient; after the distal end of the radio frequency ablation tube reaches the target lumen, measure impedance of the target lumen; locate target tissue by measuring impedance, determine the position and direction of radio frequency ablation; and then adjust a radio frequency electrode to a selected ablation area via a controller on a tube control handle, to adhere the radio frequency electrode to a vascular wall around the target tissue.

To reduce damage on the target lumen in a radio frequency ablation process, the present invention further provides a radio frequency electrode with a wall-penetrating section (a wall-penetrating section is disposed at a wall-adherence radio frequency position of the radio frequency electrode), which may penetrate or pass through a vascular wall, and reach the outside of the vascular wall to directly perform radio frequency releasing on a perivascular autonomic nerve plexus, and a specific structure thereof and a technical effect thereof are described in detail in the second embodiment and the fourth embodiment.

When the radio frequency electrode with a wall-penetrating section (for a structure of the radio frequency electrode with a wall-penetrating section, reference may be made to the following) is used, after the radio frequency electrode is adhered to a vascular wall around the target tissue, wall-penetrating is implemented, and the wall-penetrating section is inserted into the vascular wall and reaches a depth required for clinical use.

In practice, there may be one or more methods for determining whether an electrode is adhered to a wall. For example, a pressure sensor is disposed on a handle, electrode wall-adherence is determined by measuring pressure for pulling back the electrode; or a tension sensor is disposed in a guy wire section of a handle, where tension intensity measured by the tension sensor is fed back to a central processing unit, and an actual tension value is displayed. Herein, a tension intensity value range collected in animal experiments may be used as an actual operation reference.

Before radio frequency ablation is started, impedance value of each radio frequency electrode is measured one by one to find whether the impedance value is close to an impedance value of tissue, and it is determined whether there is a radio frequency electrode that is not adhered to a wall, and if yes, adjustment is performed in time and the previous step is repeated. After it is confirmed according to the impedance value that each radio frequency electrode has been adhered to a wall, a radio frequency ablation operation is started.

After the radio frequency electrode is adhered to a wall (and punctured), an electrophysiological signal (such as impedance, nerve impulse activities, or smooth muscle rhythm) may be selectively collected before radio frequency is loaded, for use of data analysis in an operation process.

(3) Generates one or more groups of guiding parameters from the database, according to the basic information of the patient input in step (1), where the guiding parameters include: radio frequency output power, radio frequency loading duration time, a set temperature, and an impedance threshold, and may also include other related information, such as an impedance change range, output power strength, and a tissue temperature change range. Each parameter in the guiding parameters may be a determined value, or may be a value range with reference value. An operation executor selects one group of guiding parameters to start a radio frequency ablation process.

(4) In the radio frequency ablation process, monitor an impedance changed of the target tissue, and adjust a radio frequency parameter accordingly, where if the effect is not ideal, another mode may be used, or fine adjustment may be performed, where parameters that may be adjusted include: the set temperature, the output power, and the radio frequency loading duration.

In the radio frequency ablation process, multiple dynamic monitoring methods are included to perform real-time monitoring, to ensure effectiveness of radio frequency ablation, and also damage on a vascular wall (a target lumen) around the target tissue is minimized. When any displayed monitoring result exceeds a critical value, radio frequency is stopped, an automatic alarm is raised, and the radio frequency parameters are recorded; otherwise, radio frequency is continued.

For example, in a real-time dynamic temperature monitoring process, by applying a temperature sensor and a temperature monitoring system device in the temperature monitoring module 4, real-time dynamic monitoring may be performed on temperature around the distal end of a tube in an operation process, tissue temperature changed may be measured, and it may be determined whether a temperature value exceeds a set threshold; if the result is no, radio frequency is continued; and if the result is yes, radio frequency is stopped, an automatic alarm is raised, and the radio frequency parameters are recorded.

In addition, real-time dynamic intra-cavity optical tomography imaging monitoring and real-time dynamic intra-cavity ultrasound imaging monitoring may be further included for imaging tissue around the target lumen, and it is determined whether temperature of the target lumen and tissue damage exceed set thresholds; if the result is no, radio frequency is continued; and if the result is yes, radio frequency is stopped, an automatic alarm is raised, and the radio frequency parameters are recorded.

(5) During the radio frequency ablation, monitor the impedance changed of the target tissue in real time or intermittently, and determine whether the impedance value of the target tissue is within a preset impedance threshold range; if the result is yes, stop radio frequency and store the radio frequency parameters; and if the result is no, repeat step (4) until the impedance value of the target tissue is within a preset impedance threshold range.

In step (5), when a determining result is yes, after radio frequency is stopped, the electrophysiological signal may further be measured again, and the electrophysiological signal and radio frequency data are associated and then stored in the database.

In addition, step (6) is further included: in a follow-up monitoring period, collect a life information index (such as blood pressure) of a patient, and associate the radio frequency data with the life information index and then store the life information index in the database, to perform estimation and automatic correction on data in the database, thereby replacing some existing guiding parameters. Such recorded patient information and radio frequency data parameters may be used for tracing treatment effects, or may be used by treatment organizations and surgeons to perform statistical analysis and optimize database information. For example, by periodically measuring blood pressure of a patient after an operation and tracing a blood pressure change of the patient after a radio frequency ablation operation, the curative effect of renal nerve removing radio frequency ablation for treatment of resistant hypertension may be determined according to these data.

The foregoing data may be used for establishing an individual file chronologically, which is permanently stored in a memory of a radio frequency ablation device to form a database, and becomes evidence traceable for a long time.

By viewing and making statistics of a large amount of individual file data in the database, optimal operation parameter intervals of patients with different backgrounds such as different nationalities, different regions, different countries, or different years may be analyzed, thereby guiding surgeons to perform operations on patient groups with different backgrounds.

Via the establishment of these methods, orientational and quantitative analysis and research may also be performed on causes and pathogenesis of hypertension patient groups, thereby determining operation methods for different patient groups.

In conclusion, in the radio frequency ablation method provided by the present invention, before an operation is started, guiding parameters may be automatically generated, for selection and use by an operation executor; in an operation process, real-time impedance monitoring, temperature monitoring, intra-cavity ultrasound imaging monitoring, and intra-cavity optical tomography imaging monitoring may be performed, to monitor and regulate the operation process. The radio frequency ablation method is a scientific and safe radio frequency ablation method with guiding significance.

In the radio frequency ablation system provided by the present invention, impedance measuring is performed on a nerve ablation part, and real-time dynamic monitoring of a target nerve to ablate is implemented, to guide control and handling of the degree of nerve ablation, thereby improving a curative effect and treatment precision, and preventing complications.

The radio frequency ablation method and the radio frequency ablation system provided by the present invention not only can be used in renal artery nerve removing radio frequency ablation for treating resistant hypertension, but also can be used in other nerve removing ablation operations, for example: renal sympathetic nerve ablation in which a renal vein is inserted via a vein for treating resistant hypertension; and renal sympathetic nerve ablation in which a renal pelvis and a renal calyx are inserted via a urinary passage, and for another example, duodenal wall-penetrating pneumogastric nerve branch radio frequency ablation of a duodenal ulcer patient, trachea/bronchus wall-penetrating pneumogastric nerve branch radio frequency ablation of an asthma patient, and percutaneous coeliac artery wall-penetrating sympathetic nerve radio frequency ablation of a diabetic patient.

First Embodiment

Besides providing the radio frequency ablation method and the radio frequency ablation system, the present invention further provides a device used for implementing the foregoing method. The radio frequency ablation device provided by the present invention is described below with reference to an example of a temperature-controlling radio frequency device provided by FIG. 4 to FIG. 10.

Figure 4:
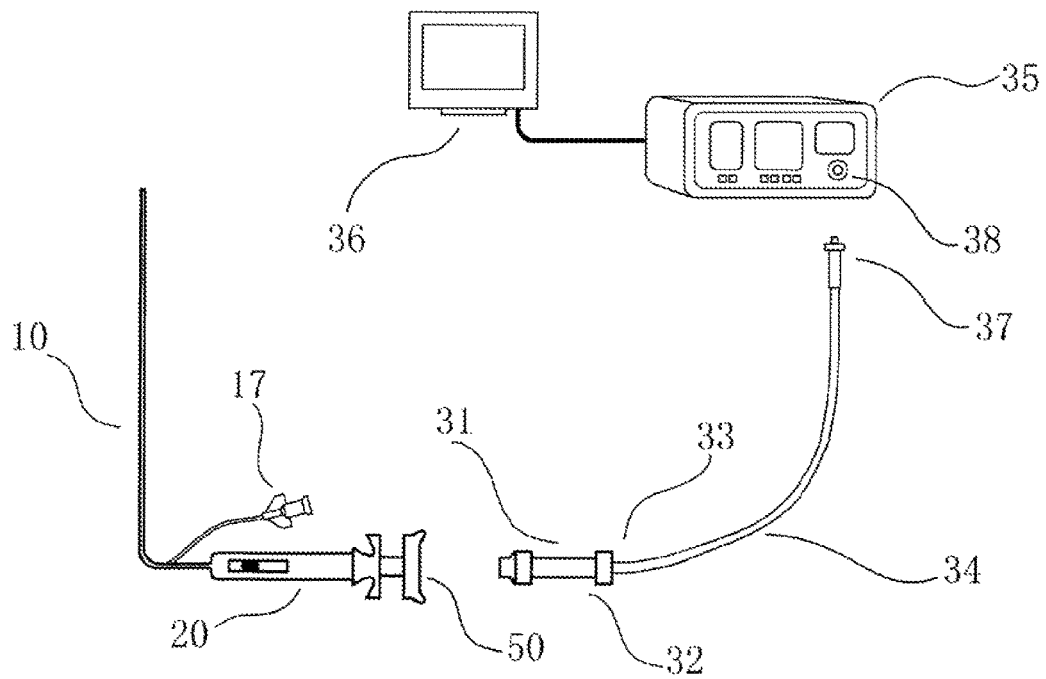
FIG. 4 is a schematic structural diagram of a temperature-controlling radio frequency device in a first embodiment of the present invention.
Figure 5:
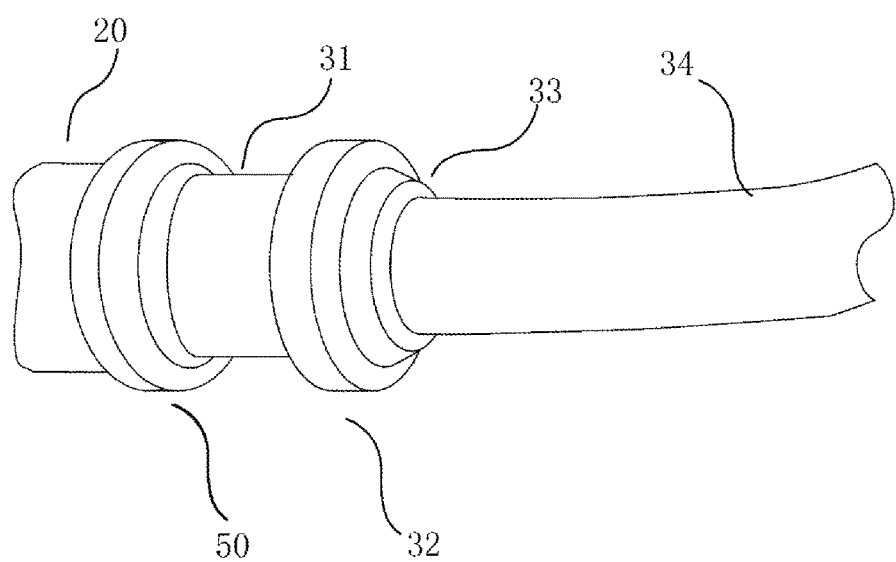
FIG. 5 is a schematic structural diagram of a composite cable in the temperature-controlling radio frequency device shown in FIG. 4.

The temperature-controlling radio frequency device shown in FIG. 4 includes a radio frequency ablation tube 10 and a control handle 20 for controlling actions of moving forward, moving backward, and bending of the radio frequency ablation tube 10, where the near end (that is, the rear end, one end away from a patient body) of the radio frequency ablation tube 10 is connected to the control handle 20, and a radio frequency electrode 12 with a wall-penetrating section is disposed at the distal end (that is, the front: one end contacting the patient body) of the radio frequency ablation tube 10, to perform ablation on target tissue of a nerve in a target lumen. A specific structure of the radio frequency electrode with a wall-penetrating section and a technical effect thereof will be described in detail in the second embodiment, the third embodiment, and the fourth embodiment.

Besides the radio frequency electrode 12, the radio frequency ablation tube 10 further at least includes two functional electrodes, that is, an impedance measuring electrode and a temperature measuring electrode. Where, one electrode may be jointly used to be connected to different processing modules to implement two functions, that is, impedance measuring and radio frequency loading. And the temperature measuring function may be implemented by using a thermocouple formed by connecting a wire manufactured by a second material to the radio frequency electrode. Reference is made to the fifth embodiment and the sixth embodiment in the following for descriptions of a radio frequency electrode with both a temperature measuring function and an impedance measuring function, which are no longer described in detail herein.

The temperature-controlling radio frequency device further includes a temperature-controlling radio frequency instrument 35 connected to a display device (which may also be referred to as a monitor device), and the temperature-controlling radio frequency instrument 35 is connected to the control handle 20 via an integrated cable. The integrated cable includes an integrated connection plug tube end 31 and a cable connection plug device end 37 that are separately disposed at the two ends of a composite cable 34, where the cable connection plug device end 37 is connected to the connection plug tube end 31 via the composite cable 34, a plug flange 32, and a composite cable joint section 33 sequentially; the cable connection plug device end 37 is used for being inserted into a temperature-controlling radio frequency instrument cable socket 38 disposed on the temperature-controlling radio frequency instrument 35 to implement a connection, and the connection plug tube end 31 is used for being inserted into an integrated joint 50 disposed at the near end of the control handle 20 to implement a connection (referring to FIG. 5).

Figure 6A:
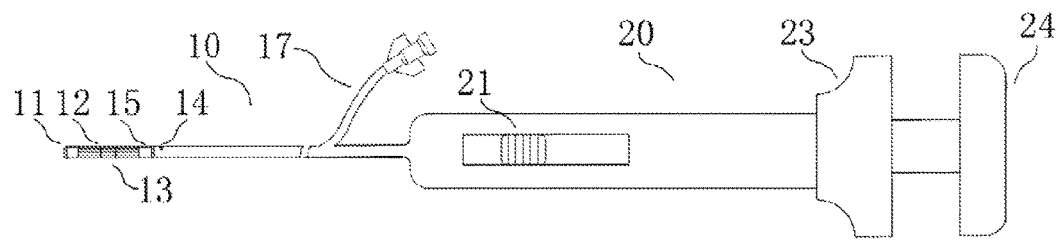
FIG. 6a is a schematic diagram of a state of a radio frequency ablation tube and a control handle thereof in the temperature-controlling radio frequency device shown in FIG. 4, when a petal-shaped radio frequency electrode is in a closed state.
Figure 6B:
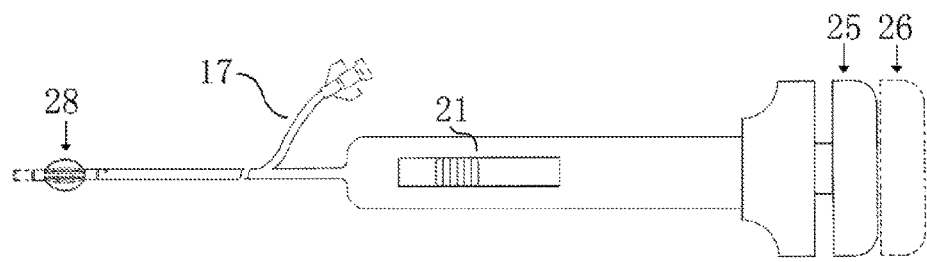
FIG. 6b is a schematic diagram of a state of a radio frequency ablation tube and a control handle thereof in the temperature-controlling radio frequency device shown in FIG. 4, when a petal-shaped radio frequency electrode is in an open state.
Figure 6C:
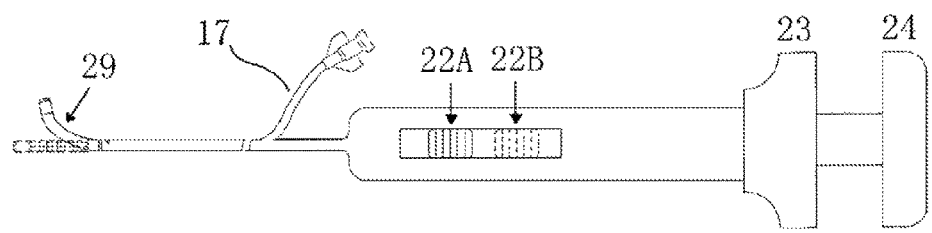
FIG. 6c is a schematic diagram of a state of a radio frequency ablation tube and a control handle thereof in the temperature-controlling radio frequency device shown in FIG. 4, when the front section of the radio frequency ablation tube is in a bent state.

FIG. 6a to FIG. 6c are separately schematic structural diagrams of a radio frequency ablation tube and a control handle thereof, when the distal end (that is, the front) of the radio frequency ablation tube is in stretched and bent states and the radio frequency electrode is in closed and open states.

Figure 7A:
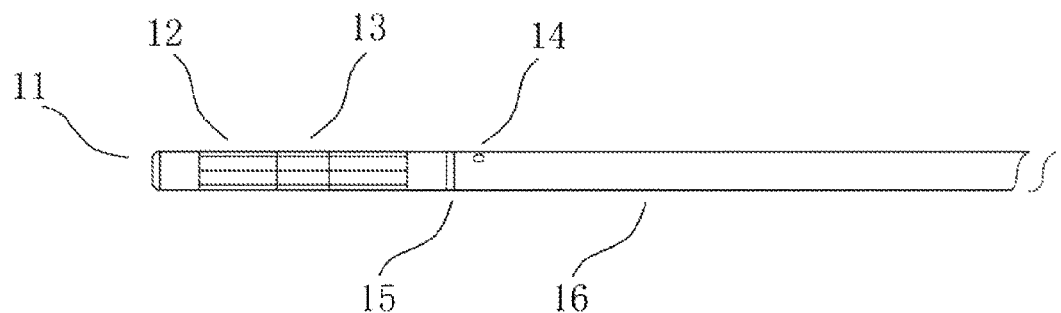
Figure 7B:
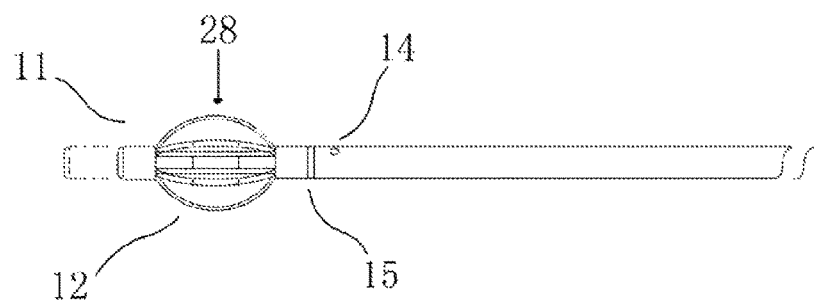
FIG. 7b is an enlarged view of the front section of a radio frequency ablation tube in the radio frequency ablation tube shown in FIG. 6b.
Figure 7C:
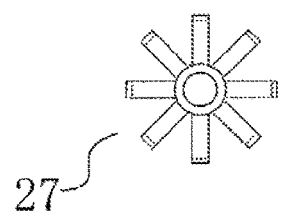
FIG. 7c is a section view of a petal-shaped radio frequency electrode of the front section of a radio frequency ablation tube in the radio frequency ablation tube shown in FIG. 6b.
Figure 8A:
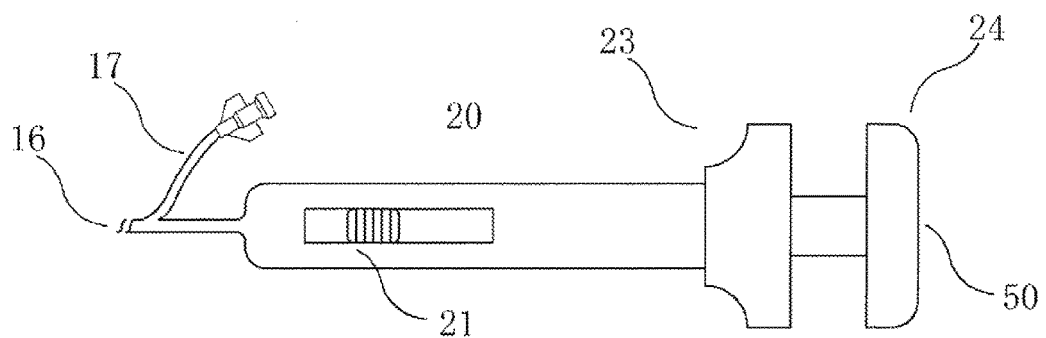
FIG. 8a is a schematic diagram of a state of a control handle in the temperature-controlling radio frequency device shown in FIG. 4, when a petal-shaped radio frequency electrode is in a closed state and the front section of the tube is in a stretched state.
Figure 8B:
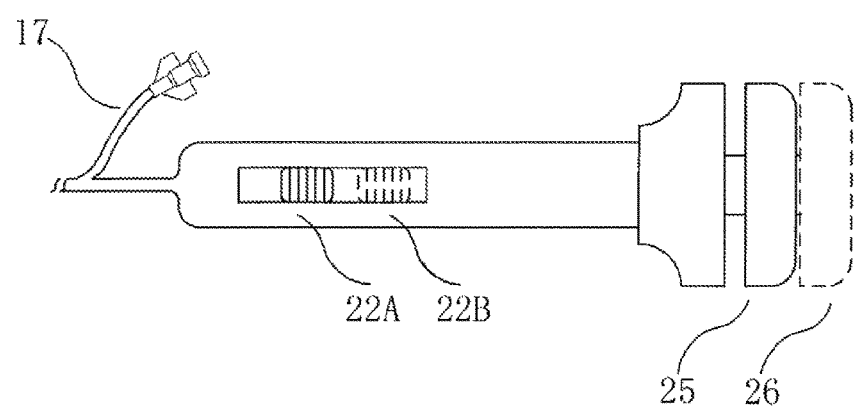
FIG. 8b is a schematic diagram of a state change of a control handle in the temperature-controlling radio frequency device shown in FIG. 4, when a petal-shaped radio frequency electrode is changed from a closed state to an open state and the front section of a tube is changed from a stretched state to a bent state.

With reference to FIG. 6a and FIG. 7a, it can be known that the radio frequency ablation tube 10 includes a tube trunk section. The near end of the tube trunk section is connected to the control handle 20, the middle section (that is, the middle section of a radio frequency electrode) of the tube trunk section carries a strip-shaped connecting electrode, the distal end section of the tube trunk section carries a radio frequency electrode 12, and a wall-penetrating section 13 is disposed at a wall-adherence radio frequency position of the radio frequency electrode 12. A specific structure and a disposing position of the wall-penetrating section 13 vary with a form change of the radio frequency electrode 12, and for a specific form example of the radio frequency electrode 12 and the wall-penetrating section 13 thereof, reference is made to the second embodiment to the fourth embodiment. The radio frequency electrode 12 is connected to a tube control handle 20 via the strip-shaped connecting electrode, and an integrated interface 50 used for being connected to the temperature-controlling radio frequency instrument 35 is disposed on the tube control handle 20.

A guide tube 16 is disposed along the length direction outside the radio frequency ablation tube 10. For disposing manners of the radio frequency ablation tube 10 and the guide tube 16, reference may be made to the drawings in the seventh embodiment to the tenth embodiment, and specific introductions thereof are as follows. The guide tube 16 is in a strip-shaped structure, and the middle section thereof is parallel to the middle section of the radio frequency electrode. The middle section of the guide tube 16 may be solid or may be hollow, and a spatial arrangement relationship between the guide tube 16 and the radio frequency electrode may be parallel, concentric or the like. When the guide tube 16 is a hollow tube, an opening 14 is disposed at the front thereof, the rear end is inserted into the control handle 20, and the guide tube 16 is diverged, at the front or rear of the control handle 20, into tube branches 17 with an interface. Through the interface at the rear of the tube branch 17, various liquids (a radiocontrast agent, a saline solution, or medicines) may be filled or various tubal monitoring instruments such as an intra-cavity ultrasound tube, a balloon tube, and an optical tomography imaging tube may be inserted. A bending control wire is disposed at the middle section of the guide tube 16 along the long axis of the guide tube 16, the front of the bending control wire is fixed to the distal end of the radio frequency electrode 12, and the rear end (that is, the near end) of the bending control wire is connected to a bending controller on the control handle 20.

In addition, at least one X-ray opaque mark is disposed at the distal end of the radio frequency ablation tube 10, to facilitate determining of the position of a tube by an operator. In the embodiment shown in FIG. 1, X-ray marks 11 and 15 are respectively disposed at the front and the rear end of the radio frequency electrode 12.

In the radio frequency ablation tube 10, the radio frequency electrode 12 is separable from the strip-shaped connecting electrode, and a basic structure thereof is that a separable connecting point (not shown) and a separable separation apparatus (not shown) are added between the radio frequency electrode 12 and the strip-shaped connecting electrode (the middle section of the radio frequency electrode). By using the connecting point, the radio frequency electrode 12 at the front and the strip-shaped electrode at the rear end are temporarily connected, and it is ensured that a wall-penetrating section of the radio frequency electrode 12 can implement wall-penetrating; after an ablation operation is finished, the radio frequency electrode is separated from the strip-shaped electrode by using the separation apparatus, so as to leave the radio frequency electrode in the lumen wall. The connecting manner and the separation apparatus match each other, and a connection-separation technology that may be used at present is: a mechanical method, a chemical method and an ionization method.

In addition, the outer surface of the radio frequency electrode 12 may carry medicines for clinical use, thereby achieving the effect of medicine administration for treatment before and after an operation. Specifically, in an existing technology where a medicine loading support is used, medicines for clinical use are coated on the surface of the radio frequency electrode, and the medicines are released on partial tissue during the radio frequency ablation, so as to increase the number of choices for and improve the effect of clinical treatment, and prevent and treat various complications such as ache, convulsion, infection, hyperplasia, and thrombosis. In addition, the wall-penetrating section may also be covered with medicines for regulating a sympathetic nerve, so as to regulate and control the sympathetic nerve. When the radio frequency electrode loaded with medicines is left in the lumen wall after being separated, the carried medicines may be slowly released in a chronic and controllable manner.

With reference to FIG. 6a to FIG. 8b, it can be known that the control handle 20 includes a tube guiding control handle 21, and a tube electrode control handle 23 and a tube electrode auxiliary control handle 24 disposed at the end of the tube guiding control handle 21. The tube guiding control handle 21 may be switched at any position between a stretched position 22A and a bent position 22B shown in FIG. 6c, to control the degree of curvature of the distal end of the radio frequency ablation tube, where the degree of curvature is between 0 and 90 degrees; the tube electrode auxiliary control handle 24 may be switched at any position between an open position 25 close to the tube electrode control handle 23 shown in FIG. 6b and a closed position 26 away from the tube electrode control handle 23, to control the degree of opening of the radio frequency electrode 12, and control a wall-penetrating action of the wall-penetrating section 13. Certainly, the wall-penetrating action of the wall-penetrating section 13 may be controlled via position switching of the tube electrode auxiliary control handle 24, or may be implemented via a wall-penetrating controller that is used for controlling the wall-penetrating section and is separately disposed on the control handle 20. In addition, a separation controller used for controlling the separation apparatus between the radio frequency electrode 12 and the strip-shaped connecting electrode to be disconnected is further disposed on the control handle 20.

As shown in FIG. 6*b*, when the tube electrode auxiliary control handle 24 is switched from the closed position 26 away from the tube electrode control handle 23 to the open position 25 close to the tube electrode control handle 23, the radio frequency electrode is switched from a closed state to an open state. For a nerve ablation tube 10 and a state change of the control handle 20, refer to FIG. 7*b* and FIG. 8*b* respectively, where the dotted line represents a closed state before switching, and the solid line represents an open state after switching. For the front view and the side view of an open state of a petal-shaped electrode, refer to states pointed by an arrow 28 in FIG. 7*b* and an arrow 27 in FIG. 7*c* respectively.

As shown in FIG. 6*c*, when the tube guiding control handle 21 is switched from the stretched position 22A to the bent position 22B, the distal end of the radio frequency ablation tube is switched from a stretched state to a bent state. For a nerve ablation tube 10 and a state change of the control handle 20, refer to FIG. 7*c* and FIG. 8*b* respectively, where the dotted line represents a stretched state before switching, and the solid line represents a bent state after switching. The distal end of the tube changes from the structure as shown by the dotted line in the figure to the structure as shown by the solid line in the figure, that is, the distal end of the tube is gradually bent from a stretched state, and for the bent state of the distal end of the tube, refer to the structure pointed by an arrow 29 in FIG. 6*c*. The tube guiding control handle 21 may be at any position between the stretched position 22A and the bent position 22B. The closer the tube guiding control handle 21 is to the bent position 22B, the larger the degree of curvature of the distal end of the nerve ablation tube 10 is, and the degree of curvature of the distal end of the nerve ablation tube 10 may change between 0 and 90°.

Figure 9:
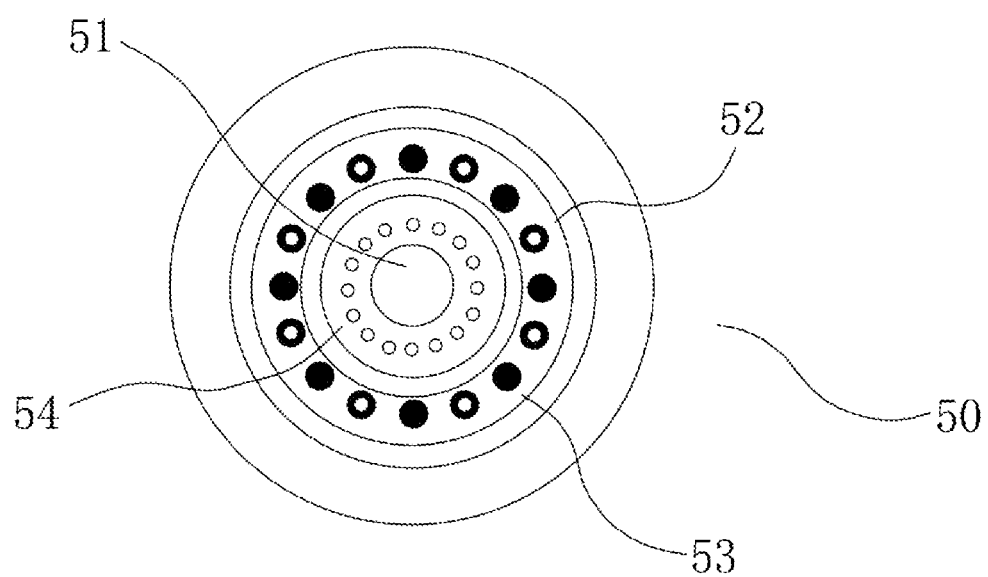
FIG. 9 is a schematic structural diagram of a coronal surface of an integrated interface of a control handle in the temperature-controlling radio frequency device shown in FIG. 4.

As shown in FIG. 9, the integrated interface 50 is disposed at the rear of the control handle 20. Specifically, a circular integrated interface 50 is disposed at the rear end of the tube electrode auxiliary control handle 24. The circular integrated interface 50 includes multiple interfaces disposed annularly, where a multiplex channel 51 is disposed at the central position, and an impedance electrode interface 52, a temperature-controlling electrode interface 53, and a radio frequency electrode interface 54 are separately disposed outside the multiplex channel 51. The impedance electrode interface 52, the temperature-controlling electrode interface 53, and the radio frequency electrode interface 54 are respectively used for connecting the impedance measuring electrode, the temperature measuring electrode, and the radio frequency electrode in the radio frequency ablation tube and corresponding functional modules inside a temperature-controlling radio frequency instrument 35.

Figure 10:
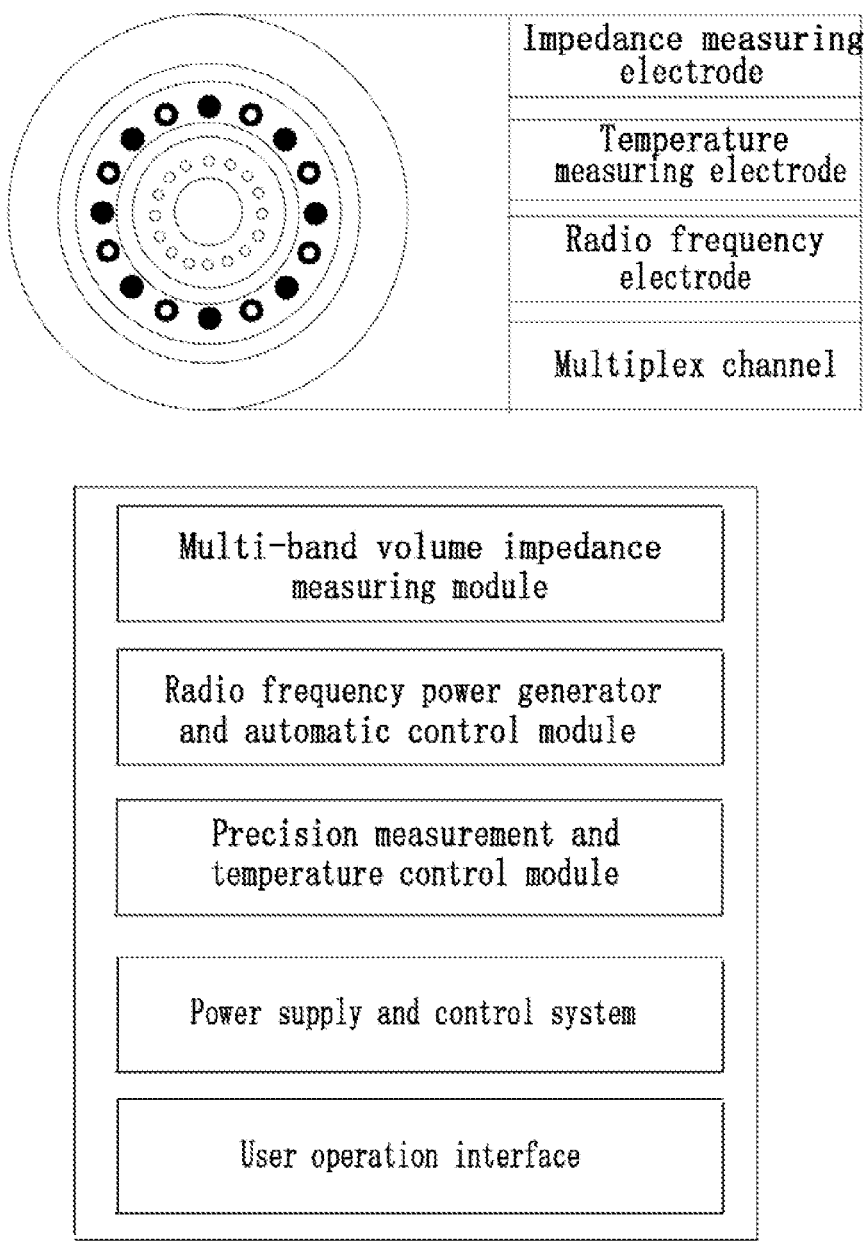
FIG. 10 is a schematic diagram of connection of the integrated interface shown in FIG. 9.

As shown in FIG. 10, in the first embodiment, a power supply and control system, a multi-band impedance measuring module, a radio frequency power generator, and automatic control module, and a precision measuring and temperature control module are mainly disposed inside the temperature-controlling radio frequency instrument 35. In addition, a user operation interface is further disposed. The multi-band impedance measuring module is connected to the impedance measuring electrode via the impedance electrode interface 52 in the integrated interface 50, the radio frequency power generator and the automatic control module are connected to the radio frequency electrode via the radio frequency electrode interface 54 in the integrated interface 50, and the precision measuring and temperature control module is connected to the temperature measuring electrode via the temperature-controlling electrode interface 53 in the integrated interface 50.

The overall structure of the radio frequency ablation device provided by the present invention is introduced above by using the first embodiment as an example. In addition, to better implement an effect of the radio frequency ablation, and reduce damage of the radio frequency ablation on non-target tissue, the present invention further makes different improvements to a radio frequency electrode, a radio frequency ablation tube, and a guide tube separately, which are separately described below with reference to the accompanying drawings.

The second embodiment, the third embodiment, and the fourth embodiment are separately three radio frequency electrodes with a wall-penetrating section, the fifth embodiment and the sixth embodiment are radio frequency electrodes with both a temperature measuring function and an impedance measuring function, the seventh embodiment and the eighth embodiment are radio frequency ablation tubes with multiple grooves on the surface, the ninth embodiment is a cable-type radio frequency ablation tube, and the tenth embodiment is a guide tube with an anti-electromagnetic interference function.

In the prior art, percutaneous renal sympathetic nerve ablation using a minimally invasive technology has been applied clinically, and achieves a desirable effect. Besides, it is found in clinical researches that, the percutaneous renal sympathetic nerve ablation still has shortcomings in a treatment process. When the percutaneous renal sympathetic nerve ablation is used for ablating a sympathetic nerve, nerve ablation is performed by inserting a radio frequency ablation tube into a renal artery and releasing heat in the renal artery by a radio frequency electrode. In one aspect, because renal sympathetic nerves are at the outermost layer of a renal vascular wall, in the process, the heat generated by the radio frequency electrode first needs to be transferred from an inner wall of a vessel to layers of a tube wall to finally reach the outer layer. A large amount of energy is lost on the vascular wall in a non-treatment area, and in order to enable sufficient energy to reach the outer layer of a vessel to implement ablation on the sympathetic nerve, an energy output of the radio frequency electrode and treatment time definitely need to be increased, and therefore, inevitable damage is caused on a partial vascular wall. In another aspect, because heat transfer of vascular wall tissue is unsatisfactory, but a blood flow rate in a renal artery is very fast, a large amount of energy generated by the radio frequency electrode in a vessel are taken away by the high speed blood flow, which seriously affects the treatment effect, and affects full exertion of the potential of the minimally invasive technology and improvement of the clinical treatment effect.

Therefore, in the second embodiment, the third embodiment, and the fourth embodiment, the present invention provides three types of radio frequency electrodes 60 with a wall-penetrating section as examples. A wall-penetrating section is disposed at a wall-adherence radio frequency position of the radio frequency electrode 60, and when ablation is implemented, the wall-penetrating section can directly penetrate or pass through a tube wall to get near perivascular autonomic nerve plexus to release energy, so that damage on non-target lumen tissue in a radio frequency ablation process can be minimized.

The front of the wall-penetrating section disposed at the wall-adherence radio frequency position of the radio frequency electrode has a sharp acute angle, and may have a blade whose shape is conic, rhombic or the like. A length range of the wall-penetrating section is preferably: 0.01 mm to 20 mm, and a diameter range of the wall-penetrating section is preferably: 0.01 mm to 2.0 mm.

The design for the radio frequency electrode to carry a wall-penetrating section may be varied, and this specification uses only the following three types of design as examples: a wall-penetrating section is disposed, in a sharp projection shape, at the wall-adherence position of the middle section of a petal-shaped radio frequency electrode; a wall-penetrating section is disposed, in a puncture needle shape, at the front of a strip-shaped puncture needle-shaped radio frequency electrode; and a wall-penetrating section is disposed, in a puncture needle shape, at the balloon wall of a balloon-shaped radio frequency electrode.

Second Embodiment

Figure 11A:
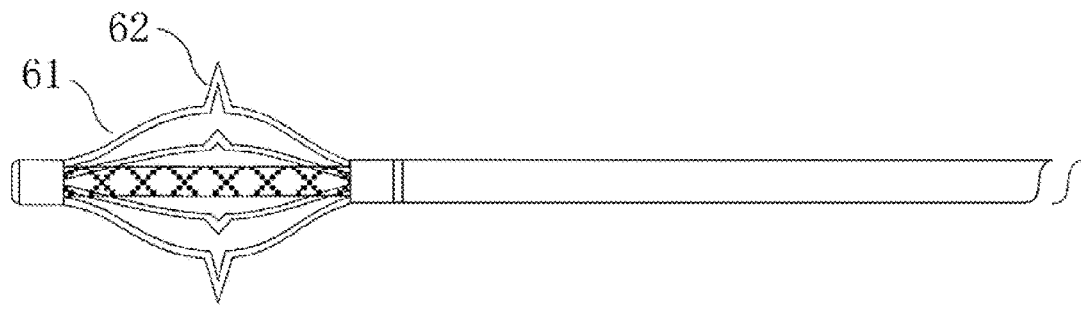
FIG. 11a is a basic schematic structural diagram of a petal-shaped cavity-passing and wall-penetrating radio frequency ablation tube with a sharp projection-shaped wall-penetrating structure in a second embodiment of the present invention.
Figure 11B:
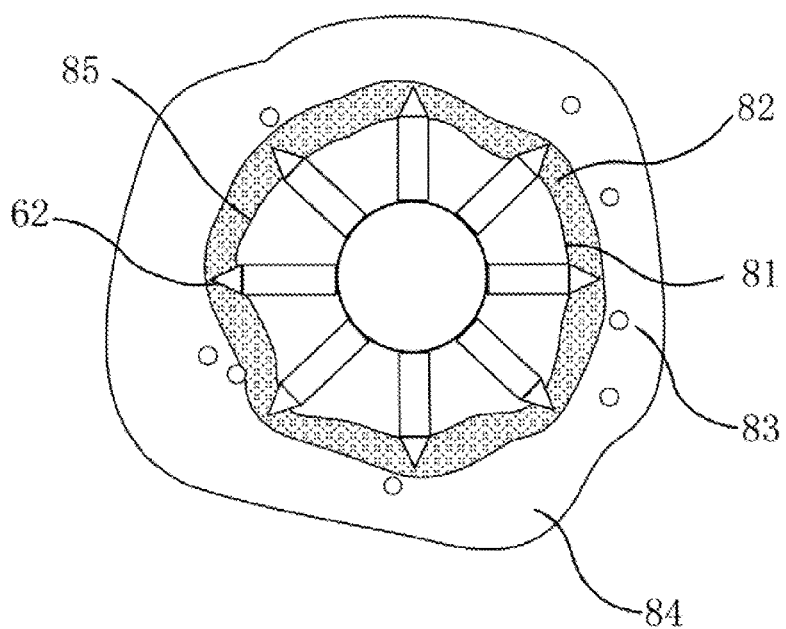

As shown in FIG. 11a and FIG. 11b, a basic structure of a petal-shaped radio frequency electrode includes a radio frequency electrode support formed by three to eight pedals of radio frequency electrodes 61, the fronts of all the radio frequency electrodes 61 are jointly welded at a common electrode welding point, to form the front of a radio frequency ablation tube, and the rear of the radio frequency electrode 61 is fixed on a tube inner wall of the radio frequency ablation tube. Each pedal of the radio frequency electrode 61 is mostly covered by an insulating layer, and only the middle section is exposed to form a radio frequency releasing point, where the radio frequency releasing point may also be used as an impedance measuring point. A sharp projection-shaped wall-penetrating section 62 is formed at a radio frequency releasing position at the middle of each pedal of the radio frequency electrode 61. When the petal-shaped radio frequency electrode is in a closed state, each pedal of the radio frequency electrode 61 is in a stretched state, and the wall-penetrating section 62 is contracted on the surface of the radio frequency electrode 61; and when the petal-shaped radio frequency electrode is in an open state, each pedal of the radio frequency electrode 61 is in a bent state and protrudes outward, and also, a sharp projection-shaped wall-penetrating section 62 is formed at the middle section of the petal-shaped radio frequency electrode, where the wall-penetrating section 62 protrudes from the surface of the radio frequency electrode 61, to penetrate or puncture a tube wall to reach a target section.

FIG. 11b is a schematic diagram of a wall-penetrating state coronal surface of the petal-shaped radio frequency electrode shown in FIG. 11a. When the petal-shaped radio frequency electrode is in an open state, the wall-penetrating section 62 penetrates or punctures a vascular intima 81 to reach a vascular smooth muscle layer 82, so as to directly release energy of a perivascular autonomic nerve plexus 83 distributed in perivascular tissue 84 to perform nerve ablation, thereby reducing damage on interior tissue of a vessel in a nerve ablation process. In a section view of a vessel shown in FIG. 11b, a blood flow part 81 in a vessel is also clearly marked. In the nerve ablation process, a sharp convex puncture section 62 of the petal-shaped radio frequency electrode 61 directly releases energy to the outside of a vascular wall, thereby avoiding the effect of flowing of blood in the vessel on the energy released by the radio frequency electrode, and the flowing of blood in the vessel also has a cooling effect on the vascular wall, thereby further reducing damage of the radio frequency releasing on the vascular wall.

Third Embodiment

Figure 12A:
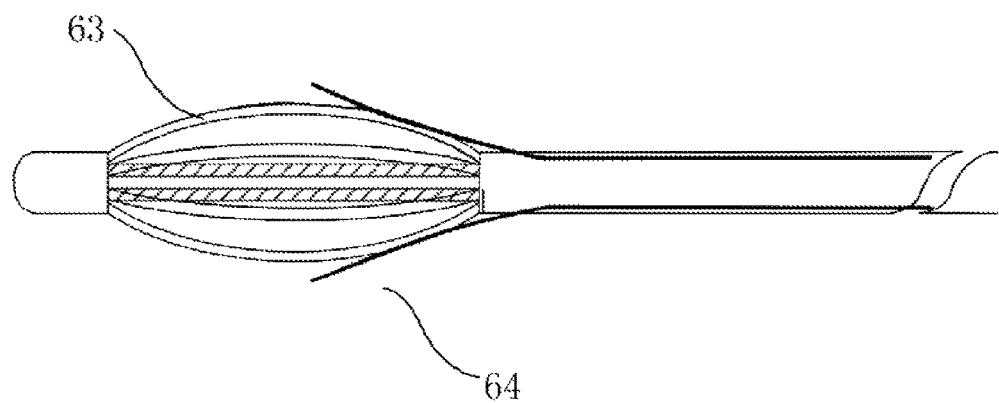
FIG. 12a is a basic schematic structural diagram of a puncture needle-shaped cavity-passing and wall-penetrating radio frequency ablation tube with a puncture needle-shaped wall-penetrating structure in a third embodiment of the present invention.

As shown in FIG. 12a, a puncture needle-shaped radio frequency electrode includes a supporting and guiding metal strip 63 and a strip-shaped puncture radio frequency electrode 64, where a wall-penetrating section is disposed at the front of the strip-shaped puncture radio frequency electrode 64. The supporting and guiding metal strip 63 is in a stretched shape when being received, and may be bent into an arched shape shown in FIG. 12a when being open. The front of the supporting and guiding metal strip 63 is fixed on a common electrode welding point, to form the front of a radio frequency ablation tube, and the rear of the supporting and guiding metal strip 63 is fixed in a tube wall of the radio frequency ablation tube.

Figure 12B:
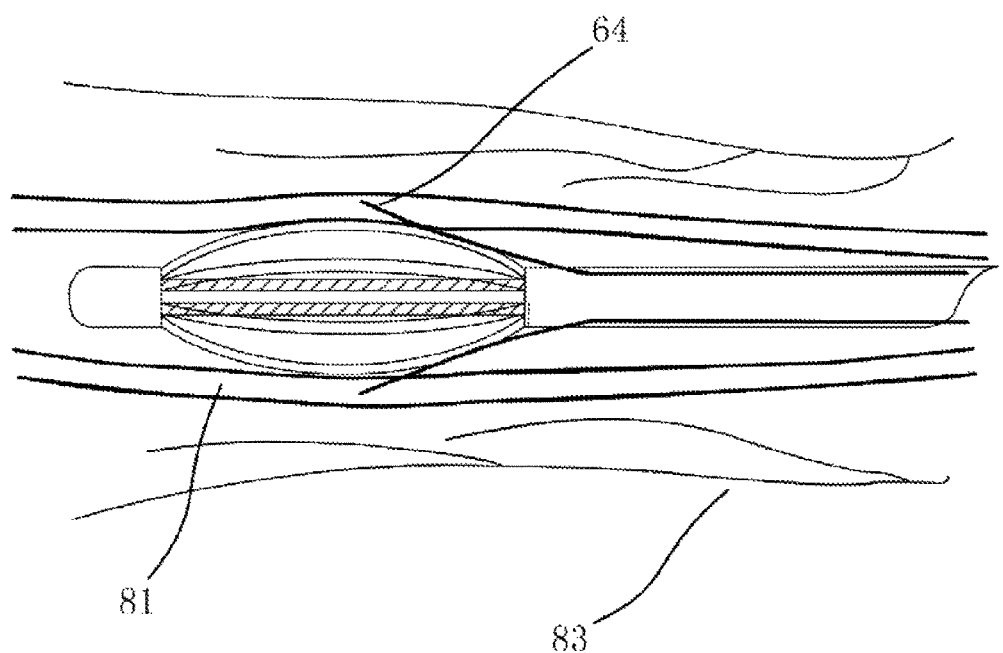

The strip-shaped puncture radio frequency electrode 64 includes a pointed section and a support section, where the pointed section is a blade-shaped wall-penetrating section disposed at the front of the strip-shaped puncture radio frequency electrode 64, and may penetrate the vascular wall. A wall-penetrating state diagram of the blade-shaped wall-penetrating section of the puncture needle-shaped radio frequency electrode is shown in FIG. 12b. The wall-penetrating section is exposed metal and forms a radio frequency releasing point; and the outside of the electrode support section is covered with an insulating material. The electrode support section is fixed with the supporting and guiding metal strip 63, and the electrode pointed section forms a free end. When the supporting and guiding metal strip 63 is open and bent into an arched shape, the electrode pointed section protrudes from the arched shape and performs wall-adherence and wall-penetrating.

Fourth Embodiment

Figure 13:
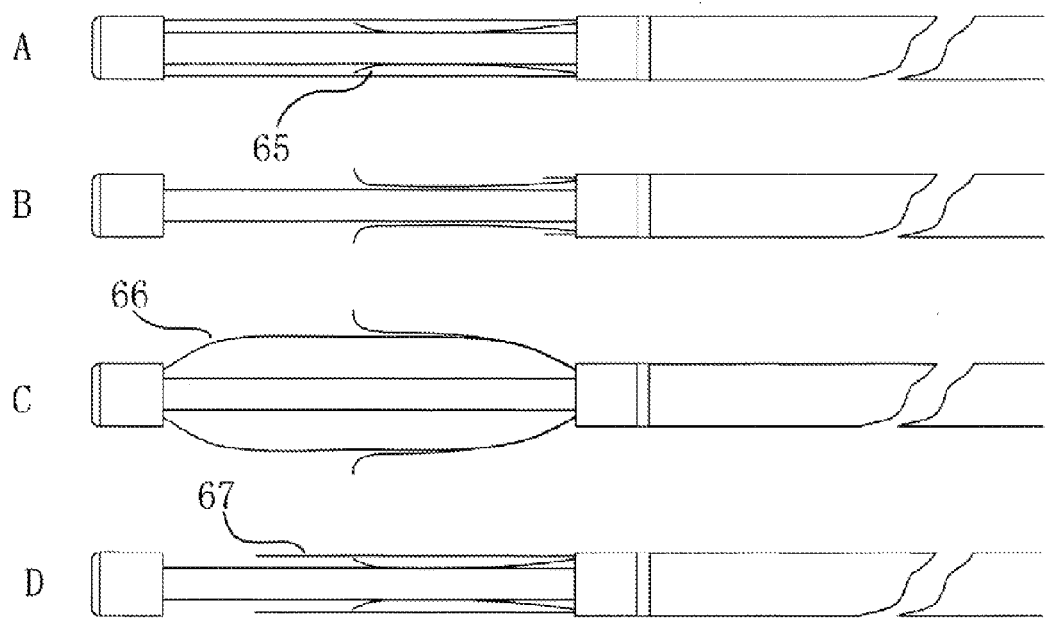
FIG. 13 is a basic schematic structural diagram of a balloon-shaped cavity-passing and wall-penetrating radio frequency ablation tube in a fourth embodiment of the present invention.
Figure 14:
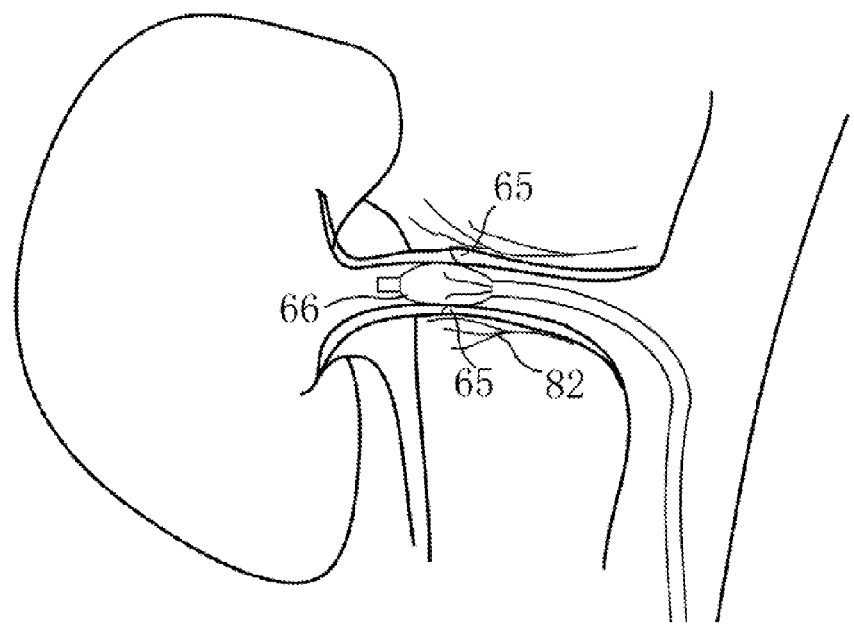
FIG. 14 is a schematic diagram of a wall-penetrating state of the balloon-shaped cavity-passing and wall-penetrating radio frequency ablation tube shown in FIG. 13.

As shown in FIG. 13, a balloon-shaped radio frequency electrode includes an electrode balloon 66, a wall-penetrating electrode 65 in which a wall-penetrating section is disposed, and an electrode protection shell 67, where the wall-penetrating section is disposed on a balloon wall outside the electrode balloon 66 to form the wall-penetrating electrode 65, and the electrode protection shell 67 is disposed outside the wall-penetrating electrode 65 in a telescopic manner. Under the effect of a telescopic control wire, the electrode balloon 66 may be switched between a closed state shown in FIG. B and an open state shown in FIG. C. The wall-penetrating electrode 65 is disposed at the outer surface of the electrode balloon 66, and when the electrode balloon 66 is open, the wall-penetrating electrode 65 protrudes from the surface of the electrode balloon 66, and the wall-penetrating section thereof penetrates a vascular wall (referring to FIG. 14). The electrode protection shell 67 is disposed outside the wall-penetrating electrode 65, and when the electrode balloon 66 is in a closed state, the wall-penetrating electrode 65 is contracted at the surface of the electrode balloon 66, and the electrode protection shell 67 is closed to receive the wall-penetrating electrode 65 and the electrode balloon 66, so as to prevent the vascular wall from being accidentally damaged by the wall-penetrating electrode 65 in processes of inserting and withdrawing a radio frequency ablation tube.

FIG. 13 shows an entire action flow of a balloon-shaped radio frequency electrode, where FIG. A is a schematic structural diagram of a balloon electrode tube in a closed state, FIG. B is a schematic structural diagram of a wall-penetrating electrode 65 and an electrode balloon 66 that are in closed states and are exposed after an electrode protection shell 67 is removed, FIG. C is a schematic structural diagram of an electrode balloon 66 in an open state, and FIG. D is a schematic structural diagram when the wall-penetrating electrode 65 and the electrode balloon 66 are in closed states again and the electrode protection shell 67 is in a closing process.

After the balloon-shaped radio frequency electrode reaches a target lumen, the electrode protection shell 67 is removed first, the electrode balloon 66 is open, the wall-penetrating electrode 65 is adhered to a wall and penetrates the wall, and radio frequency releasing is then performed. After a radio frequency process ends, the electrode balloon 66 is closed, the wall-penetrating electrode 65 is contracted on the surface of the electrode balloon 66, the electrode protection shell 67 is closed again to prevent the vascular wall from being accidentally damaged by the wall-penetrating electrode 65, and then the radio frequency ablation tube is withdrawn.

The foregoing third embodiment, fourth embodiment, and fifth embodiment separately are examples of a radio frequency electrode with a puncture section, and may further have other variations in actual use, which are not listed herein.

Figure 15A:
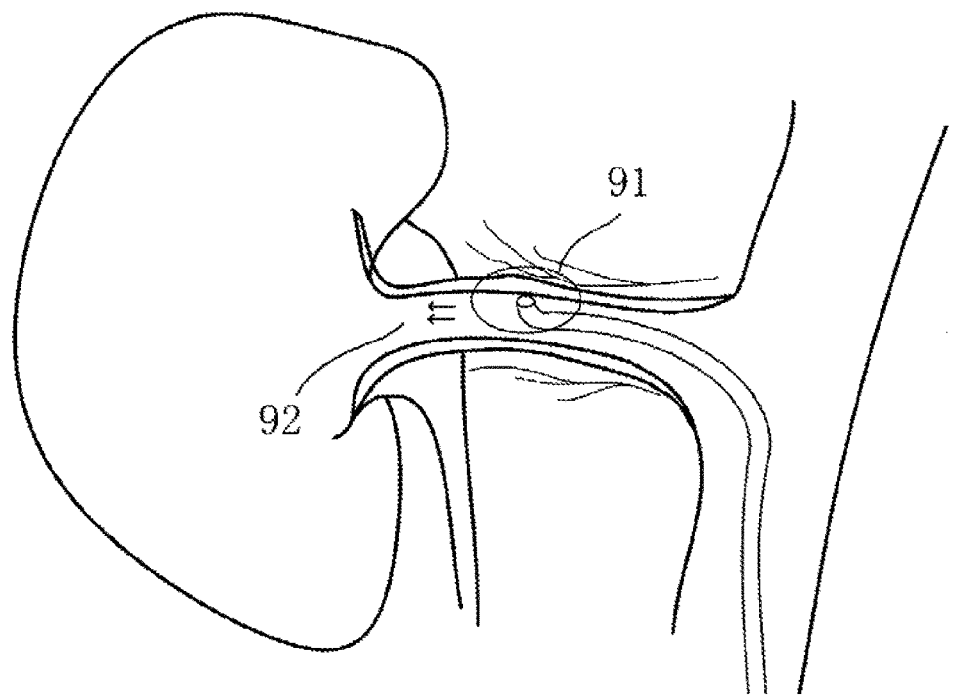
FIG. 15a is a schematic diagram of temperature transfer of percutaneous renal sympathetic nerve ablation in the prior art.
Figure 15B:
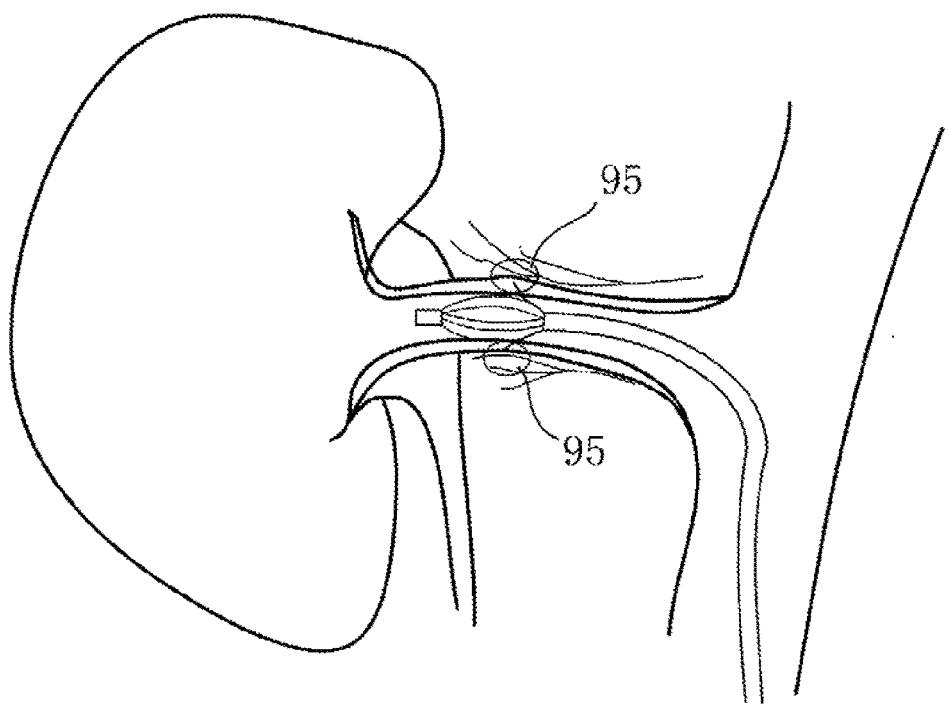
FIG. 15b is a schematic diagram of temperature transfer in a cavity-passing and wall-penetrating nerve ablation method provided by the present invention.

The effect on energy releasing in a nerve ablation process when a wall-penetrating section is disposed on a radio frequency electrode is introduced below with reference to FIG. 15*a* and FIG. 15*b*. FIG. 15*a* and FIG. 15*b* separately are schematic comparison diagrams of temperature transfer in an existing ablation technology and temperature transfer in a wall-penetrating ablation electrode provided by the present invention.

FIG. 15*a* clearly gives a single-point radio frequency electrode heat distribution area 91 and a blood-flow heat dilution direction 92 in intra-cavity radio frequency ablation, where an intra-cavity radio frequency releasing point is at the center of the flowing of blood, and most of the heat released by radio frequency is taken away directly by the flowing of blood, and only a part of diluted heat passes through the vascular wall to reach perivascular tissue 84.

In cavity-passing and wall-penetrating radio frequency ablation provided by the present invention, for the position of a radio frequency releasing point of the cavity-passing and wall-penetrating radio frequency ablation, refer to a puncture radio frequency electrode heat distribution area 95 in FIG. 15*b*. A wall-penetrating section is disposed on the radio frequency electrode to push the radio frequency releasing point from a vascular lumen to a tube wall, thereby causing fundamental changes on heat energy conduction: 1. The radio frequency electrode is implanted in tissue of the tube wall to perform ablation, so that the radio frequency electrode approaches an autonomic nerve plexus around the vascular wall more effectively, which remarkably shortens a diffusion distance and time of heat energy in the tube wall, also reduces a diffusion range of heat energy in the tissue of the tube wall, improves the curative effect, and reduces damage caused by radio frequency releasing on partial tissue in the tube wall. 2. Because the radio frequency electrode releases energy in the tissue of the tube wall, the disadvantage that an intra-cavity blood flow may quickly take away heat energy of the radio frequency electrode is eliminated, and the present invention allows and uses the intra-cavity quick blood flow to take away heat energy of an inner layer of the vascular wall, which can implement more effective protection on the tube wall without affecting accumulation of heat energy in tissue of an outer layer of the vascular wall, so that less heat energy and shorter time may be used clinically to achieve the treatment effect, and make the treatment more effective.

The radio frequency ablation device provided by the present invention is introduced above, and the cavity-passing and wall-penetrating nerve ablation is introduced below by using percutaneous renal artery wall-penetrating sympathetic nerve radio frequency ablation as an example.

By using a Seldinger method, a vessel is punctured and a vaginae vasorum is placed, a guide tube is then inserted via the vaginae vasorum to reach a renal artery, and a cavity-passing and wall-penetrating nerve ablation tube is then inserted from the outer interface of the guide tube. After the front of the radio frequency ablation tube enters the renal artery, a impedance monitoring system is started first to measure impedance of a lumen before an operation via a electrical impedance electrode, to determine an ideal ablation area or ablation point. After an ablation part is determined, a tube controller on a control handle is used for adhering the radio frequency electrode to a wall, that is, making the ablation electrode close to an inner wall of the lumen of the ablation part; and then a wall-penetrating controller on the control handle is used for pushing the wall-penetrating section to implement a wall-penetrating action, so that the wall-penetrating section of the front of the radio frequency ablation tube punctures the lumen wall through the lumen, where the puncture depth may be controlled and selected according to clinical use, and the design requirement is to make, in a allowable range for integrity and impermeability of the tube wall, the ablation electrode as close as possible to target tissue—a nerve that needs to be ablated. After the wall-penetrating section reaches a preset depth, a nerve ablation system with automatic temperature-controlling radio frequency is started, radio frequency energy emitted by the system reaches perivascular tissue via the radio frequency electrode and the wall-penetrating section, and the perivascular tissue absorbs the radio frequency energy and generates heat, having an ablation effect on surrounding nerves. Because the wall-penetrating ablation electrode is used, compared with the prior art, radio frequency energy requirements for achieving the clinical treatment effect is lower, time is shorter, and damage on the partial lumen wall is also less severe. In addition, the wall-penetrating section may form a fibrotic scar around a puncture needle track, to close the needle track automatically, thereby ensuring integrity and impermeability of the lumen.

During the radio frequency ablation, a impedance monitoring system may be started in real time or intermittently, to monitor impedance of an ablation area, so as to guide and determine whether to continue or stop radio frequency ablation. After the ablation satisfies a clinical requirement, radio frequency emission is stopped, and the wall-penetrating controller on the control handle is then operated to enable the wall-penetrating ablation electrode to return to the lumen and to be contracted into the ablation tube, and then the tube is withdrawn to complete the operation.

Besides the foregoing steps, the wall-penetrating radio frequency ablation tube disclosed by the present invention may further perform medicine loading on the radio frequency electrode and partial implantation, to provide more clinical choices and perform more effective and safe renal sympathetic nerve radio frequency ablation. The radio frequency emission is stopped after the ablation satisfies the clinical requirement, then the separation controller on the control handle is operated to disconnect a separation apparatus between the radio frequency electrode and the strip-shaped connecting electrode, so that the radio frequency electrode is left in the lumen wall, and then the tube is withdrawn to complete the operation. Medicines carried on the outer surface of the radio frequency electrode are released on partial tissue during the radio frequency ablation, so as to increase the number of choices for and improve the effect of clinical treatment, and prevent and treat various complications such as ache, convulsion, infection, hyperplasia, and thrombosis. In addition, after the wall-penetrating ablation electrode loaded with medicines is separated and left in the lumen wall, the carried medicines may be slowly released in a chronic and controllable manner, to achieve regulation and control on the sympathetic nerve.

Fifth Embodiment

In a radio frequency device, a radio frequency electrode is a key component used for contacting or approaching human tissue to be treated and performing radio frequency energy releasing. The radio frequency electrode is used for converting a radio frequency signal into a temperature field, to treat human tissue via a heat effect.

To implement real-time monitoring in a radio frequency process, the present invention further provides a radio frequency electrode that can simultaneously implement radio frequency releasing, impedance measuring, and temperature measuring. A basic function of the radio frequency electrode is radio frequency releasing, and by measuring impedance of a radio frequency releasing point of the radio frequency electrode, the impedance measuring function can be implemented. In addition, a second material is connected to the radio frequency electrode, where the second material refers to a material different from the material used for forming the radio frequency electrode, so that the radio frequency electrode and the second material form a temperature measuring thermocouple, and temperature is measured by measuring a current value at a connection interface between the radio frequency electrode and the second material. To improve accuracy of temperature monitoring in a radio frequency operation process, a connection position of the second material is disposed near the radio frequency releasing point.

Figure 16:
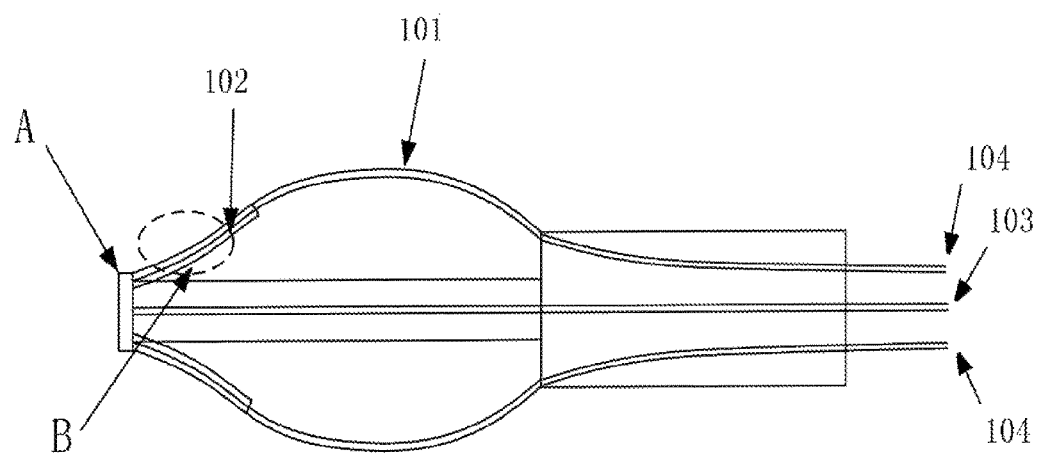
FIG. 16 is a schematic structural diagram of a petal-shaped radio frequency electrode with both a temperature measuring function and an impedance measuring function in a fifth embodiment of the present invention.

FIG. 16 shows a petal-shaped radio frequency electrode that may implement three functions simultaneously. In this embodiment, a nickel-titanium alloy is used for forming a petal-shaped radio frequency electrode support, where the radio frequency electrode support is formed by three to eight pedals of radio frequency electrodes 101, the fronts of all the radio frequency electrodes 101 are jointly welded at a common electrode welding point, a point A, to form the front of a radio frequency ablation tube, and the rear of the radio frequency electrode 101 is fixed on a tube inner wall of the radio frequency ablation tube. Each pedal of the radio frequency electrode 101 is mostly covered by an insulating layer, and only a part is exposed to form a radio frequency releasing point, where the radio frequency releasing point is also used as an impedance measuring point. The radio frequency electrode 101 is partially connected to a second material 102, that is, a copper-zinc alloy, and the second material 102, that is, the copper-zinc alloy, is connected near the radio frequency releasing point. As shown in FIG. 16, in this embodiment, the copper-zinc alloy is connected to the front of the radio frequency electrode, that is, a nickel-titanium alloy, and is close to the common electrode welding point, that is, the point A. When temperature is measured, a temperature value is obtained through calculation by collecting a current value at a connection interface B (referring to an area pointed by an arrow in a dotted circle in FIG. 16) between the nickel-titanium alloy and the copper-zinc alloy.

The form of the petal-shaped radio frequency electrode support manufactured by the nickel-titanium alloy may restore a bent and raised state by molding a shape under a body temperature condition, so as to adhere the radio frequency releasing point on the support to a vascular wall around the target tissue. A guide tube is disposed outside the radio frequency ablation tube, and when a radio frequency ablation operation is implemented, the front of the guide tube is first inserted into a target lumen, and the radio frequency ablation tube is inserted into the guide tube. Limited by the lumen of the guide tube, the petal-shaped radio frequency electrode support 101 in this case is compressed in the guide tube and conveyed all the way to the front of the guide tube. After the guide tube of the petal-shaped radio frequency electrode support 101 is exposed, under the effect of body temperature, the nickel-titanium alloy starts to restore the shape when being molded, and the radio frequency releasing point is driven to be adhered to a wall, thereby creating conditions for radio frequency ablation. After the operation ends, the radio frequency ablation tube is withdrawn to the guide tube, and because of the limitation of the lumen of the guide tube, the open petal-shaped radio frequency electrode support is straightened and narrowed, until being withdrawn from the body.

In this embodiment, the radio frequency electrode 101 is connected to a temperature-controlling radio frequency instrument separately via an effect wire 104 and a common ground wire 103. In addition, the radio frequency electrode 101 and the second material 102 are separately connected to a wire, and the wire is connected to a temperature collecting module in the temperature-controlling radio frequency instrument. Temperature is measured by collecting and measuring an induced current in a circuit.

It can be known from the above description that, under a body temperature condition, the petal-shaped radio frequency electrode support formed by the nickel-titanium alloy may restore an arched shape after being molded, so that the radio frequency releasing point on the petal-shaped electrode is closely adhered to a vascular wall. The nickel-titanium alloy is mostly covered by an insulating layer (for example, polytetrafluoroethylene), and only a part of exposed metal forms the radio frequency releasing point. In addition, in the embodiment, a thermocouple principle is used for welding a temperature sensor formed by a metal copper-zinc alloy onto the nickel-titanium alloy, an interface formed between the nickel-titanium alloy and the copper-zinc alloy generates different degrees of currents with the change of temperature, and temperature is measured by collecting the current value. Because the exposed nickel-titanium alloy has an impedance measuring capability, body impedance may be directly measured by using a measurement loop formed by the radio frequency electrode. However, when impedance is measured, an impedance measuring error caused by a temperature measuring current of a metal interface needs to be eliminated.

Sixth Embodiment

Figure 17A:
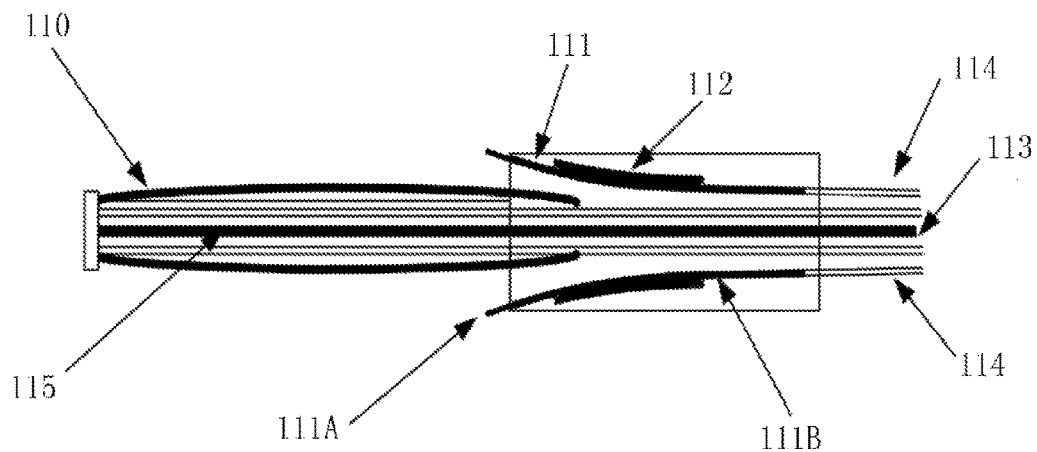
FIG. 17a is a schematic structural diagram of a puncture needle-shaped radio frequency electrode with both a temperature measuring function and an impedance measuring function in a sixth embodiment of the present invention.
Figure 17B:
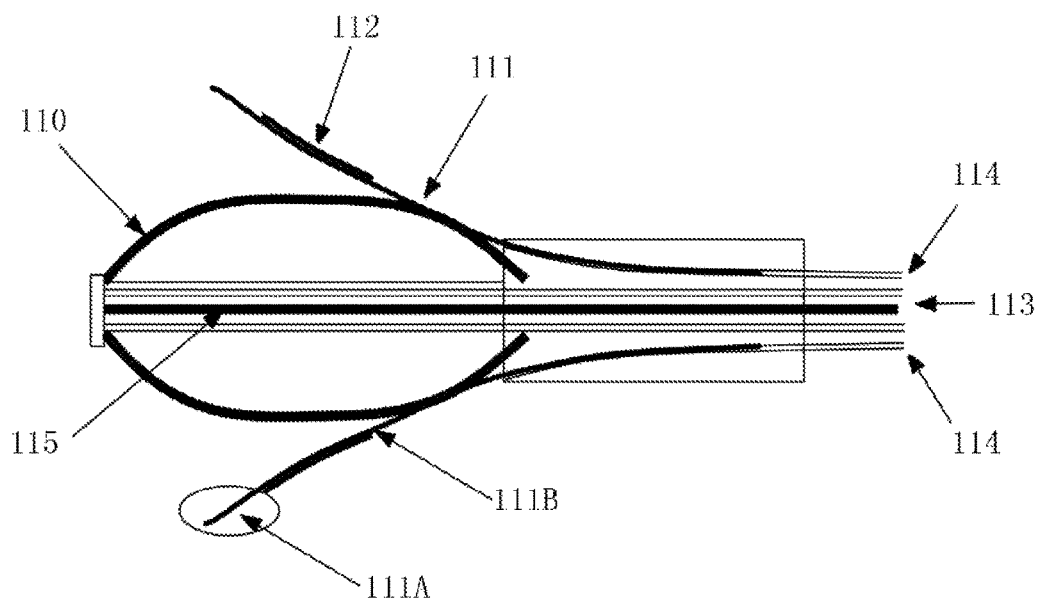

For a closed state of the puncture needle-shaped radio frequency electrode that implements three functions simultaneously, reference is made to FIG. 17a, and for an open puncture state, reference is made to FIG. 17b.

The puncture needle-shaped radio frequency electrode shown in FIG. 17a includes a supporting and guiding metal strip 110, a puncture radio frequency electrode 111, a second material 112 connected to the puncture radio frequency electrode 111, a common ground wire 113, an effect wire 114, and a telescopic control wire 115.

The supporting and guiding metal strip 110 is in a straight line shape shown in FIG. 17a when being closed, and the supporting and guiding metal strip 110 may be bent into an arched shape shown in FIG. 17b when being open. The front of the supporting and guiding metal strip 110 is fixed on a common electrode welding point, to form the front of a radio frequency ablation tube, and the rear of the supporting and guiding metal strip 110 is fixed in a tube wall of the radio frequency ablation tube.

The puncture radio frequency electrode 111 includes a pointed section 111A and a support section 111B. In the embodiment shown in FIG. 17a, an electrode pointed section 111A is exposed metal, and forms a radio frequency releasing point, and the pointed section 111A is also a wall-penetrating section of the puncture radio frequency electrode 111; and the outside of the electrode support section 111B is covered with an insulating material. The electrode support section 111B is fixed with the supporting and guiding metal strip 110, and the electrode pointed section 111A forms a free end. When the supporting and guiding metal strip 110 is open and bent into an arched shape, the electrode pointed section 111A protrudes from the arched shape and contacts a vascular endothelium.

The puncture radio frequency electrode 111 is connected to the second material 112, and the second material 112 is connected near the pointed section 111A of the puncture radio frequency electrode 111, and is close to the radio frequency releasing point. When the puncture radio frequency electrode 111 releases radio frequency, temperature near the puncture radio frequency electrode 111 changes, and in this case, a potential difference exists on a connection interface between the puncture radio frequency electrode 111 and the second material 112, and a temperature value is obtained through calculation by collecting a current value at the connection interface between the puncture radio frequency electrode 111 and the second material 112.

Certainly, besides the pointed section 111A, an exposed radio frequency releasing point may also be disposed on the electrode support section 111B of the puncture radio frequency electrode 111, and therefore, according to different disposing positions of the radio frequency releasing point, the second material 112 may also be disposed on the support section 111B of the puncture radio frequency electrode 111.

In the puncture needle-shaped radio frequency electrode, the supporting and guiding metal strip 110 is formed by a non-memory alloy. To open the supporting and guiding metal strip 110, a telescopic control wire 115 is disposed in the puncture needle-shaped radio frequency electrode, where the front of the telescopic control wire 115 is fixed with a common electrode welding point of the front of the radio frequency electrode, and the rear passes through the radio frequency ablation tube and is connected to a control handle. In use, the supporting and guiding metal strip 110 is open by pulling the telescopic control wire 115.

The telescopic control wire 115 is manufactured by a metal wire with certain hardness. When the control handle is used for pushing the control wire forward, because the supporting and guiding metal strip is contracted by the traction of pushing the radio frequency ablation tube to move forward, this telescopic state facilitates insertion of the radio frequency ablation tube into a target lumen. When the radio frequency ablation tube reaches the target lumen, the telescopic control wire 115 is pulled backward by the control handle, and because of the traction of the front of the radio frequency ablation tube, the supporting and guiding metal strip 110 is converted from a contracted state into an open state. In this case, the supporting and guiding metal strip 110 is lifted outward to adhere the puncture needle-shaped puncture radio frequency electrode 111 to a wall, thereby creating conditions for radio frequency ablation. After an operation ends, the supporting and guiding metal strip 110 is contracted by pushing the control handle forward, thereby facilitating smooth withdrawal of the radio frequency ablation tube from the body.

In this embodiment, the radio frequency electrode 111 is connected to a temperature-controlling radio frequency instrument separately via an effect wire 114 and a common ground wire 113. In addition, the radio frequency electrode 111 and the second material 112 are separately connected to a wire, and the wire is connected to a temperature collecting module in the temperature-controlling radio frequency instrument. Temperature is measured by collecting and measuring an induced current in a circuit.

In conclusion, the radio frequency electrode in the fifth embodiment and the sixth embodiment implements three functions simultaneously: radio frequency ablation, temperature measuring, and impedance measuring. Specifically, the radio frequency electrode originally has a radio frequency releasing function and an impedance measuring function, and a thermocouple is formed by welding a second material on the surface of the radio frequency electrode, so that a temperature measuring function is also implemented. A radio frequency ablation system is formed by using the radio frequency electrode, so that a temperature sensor and an impedance sensor disposed near the radio frequency electrode in the prior art can be omitted, thereby improving the overall flexibility of the radio frequency electrode and facilitating control of a radio frequency ablation process.

It should be particularly noted that, in the fifth embodiment, the radio frequency electrode support is formed by a nickel-titanium alloy, and because the nickel-titanium alloy is a memory alloy, when the radio frequency electrode support is at proper temperature, the radio frequency electrode support may restore an original fixed shape, for example, restore an arched shape in a body temperature condition, thereby implementing contact and attachment between the radio frequency electrode 101 and a target lumen. Therefore, in the fifth embodiment, there is no need to dispose a lead wire used for pulling the radio frequency electrode support to deform radio frequency electrode support, thereby simplifying the structure of the electrode. Certainly, the radio frequency electrode 101 may also be formed by using another memory alloy such as a copper-nickel alloy or a titanium alloy. When the radio frequency electrode support is formed by using another alloy except the memory alloy, only a lead wire used for pulling the radio frequency electrode support to implement bulging needs to be disposed in the radio frequency ablation tube, and for a disposing manner of the lead wire, reference may be made to the disposing of the telescopic control wire 115 in the sixth embodiment. Therefore, the material used in the present invention to form the radio frequency electrode 101 is not limited to the memory alloy, as long as the radio frequency electrode 101 is formed by a tensile material, such as a memory alloy or metal. Likewise, in the foregoing embodiments, a temperature measuring thermocouple is formed by a copper-zinc alloy used as a second material 102 and the nickel-titanium alloy. Certainly, another material such as a pure copper or a platinum alloy or a nickel-chromium alloy may also be used, as long as the material of the second material 102 is different from the material of forming the radio frequency electrode support.

Similarly, the shape of the radio frequency electrode is not limited to the shapes provided in the embodiments. Besides the petal shape provided in the fifth embodiment and the puncture needle shape provided in the sixth embodiment, the shape of the radio frequency electrode may also be another shape, for example, a balloon shape. That is, the original shape of the radio frequency electrode has no effect on implementing the three functions simultaneously. In actual use, the radio frequency electrode provided by the present invention may be formed in any shape in the prior art.

The foregoing fifth embodiment and sixth embodiment separately introduce the structure of the radio frequency electrode with both a temperature measuring function and an impedance measuring function provided by the present invention. In foregoing introductions, it is mentioned that the second material is connected to the radio frequency electrode, where there may be multiple choices of a connecting manner of the second material, for example, any one of welding, electroplating, sleeve joint, and pressure jointing is used for implementing connection. Certainly, other connecting manners not listed herein are also not excluded.

Figure 18A:
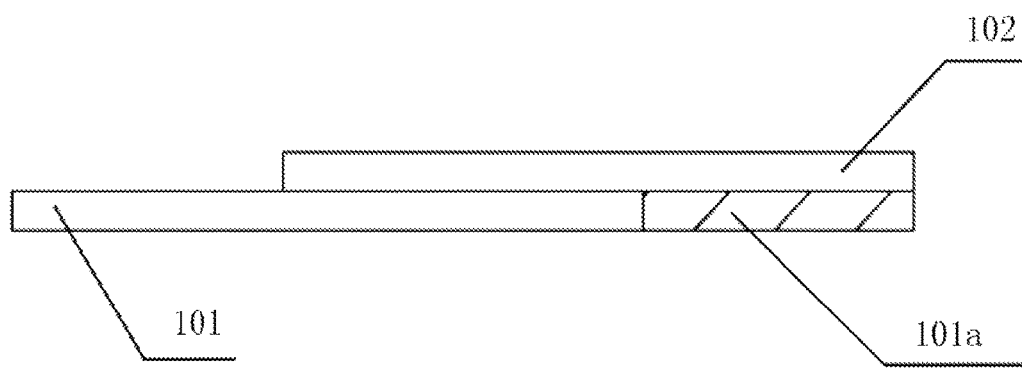
FIG. 18a is a schematic principle diagram in which a second material is connected to a radio frequency electrode in an electroplating manner.
Figure 18B:
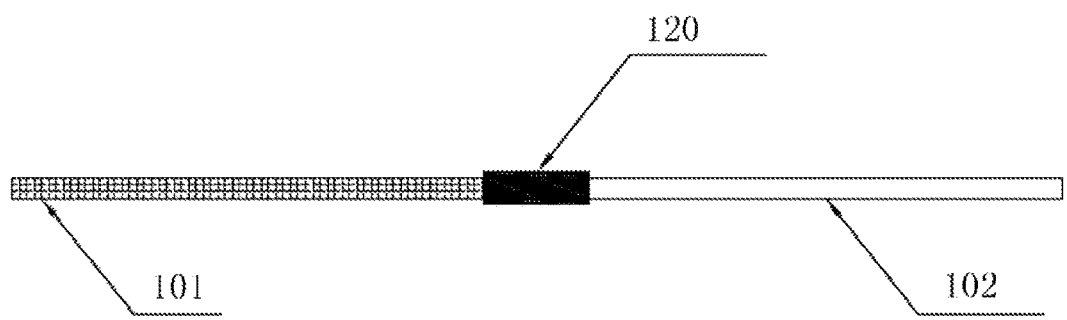
FIG. 18b is a schematic principle diagram in which a second material is connected to a radio frequency electrode in a sleeve joint manner.
Figure 18C:
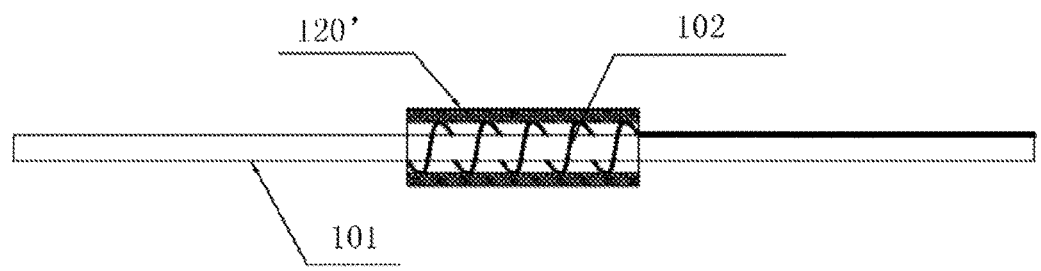
FIG. 18c is a schematic principle diagram in which a second material is connected to a radio frequency electrode in a pressure jointing manner.

To ensure accuracy of temperature measuring, the performance of the connection between the second material 102 and the radio frequency electrode 101 needs to meet a high requirement. For example, when a welding manner is used for connection, to ensure cleanness of a welding surface, the second material 102 and the radio frequency electrode 101 may be welded in a pressure welding manner. Other connecting manners are shown in FIG. 18a to FIG. 18c. An electroplating manner is shown in FIG. 18a, where a part of backing material 101a on the radio frequency electrode 101 is removed first, and then the second material 102 is grown in-situ on the electrode material whose backing material is removed. A sleeve joint manner is shown in FIG. 18b, where the radio frequency electrode 101 is connected to the second material 102 by using a connector 120, and the radio frequency electrode 101 and the second material 102 contact closely inside the connector 120. A pressure jointing manner is shown in FIG. 18c, where the second material 102 is wound around the radio frequency electrode 101, a metal ring 120' is sleeved on the outside of the radio frequency electrode 101, and finally the metal ring 120' is pressure jointed on the second material 102 by an external force, to implement the connection between the second material 102 and the radio frequency electrode 101. For an example of the radio frequency electrode with both a temperature measuring function and an impedance measuring function that is formed in the pressure jointing manner, and a manufacturing method thereof, reference may be made to introductions in the tenth embodiment, which are not described again herein. The foregoing four connecting manners belong to illustrations, and do not constitute limitations to the connection between the second material 102 and the radio frequency electrode 101.

The radio frequency electrode provided by the present invention is described above, and a structure and a measuring principle of a temperature-controlling radio frequency instrument connected to the radio frequency electrode are described below with reference to FIG. 19 to FIG. 22b.

Figure 19:
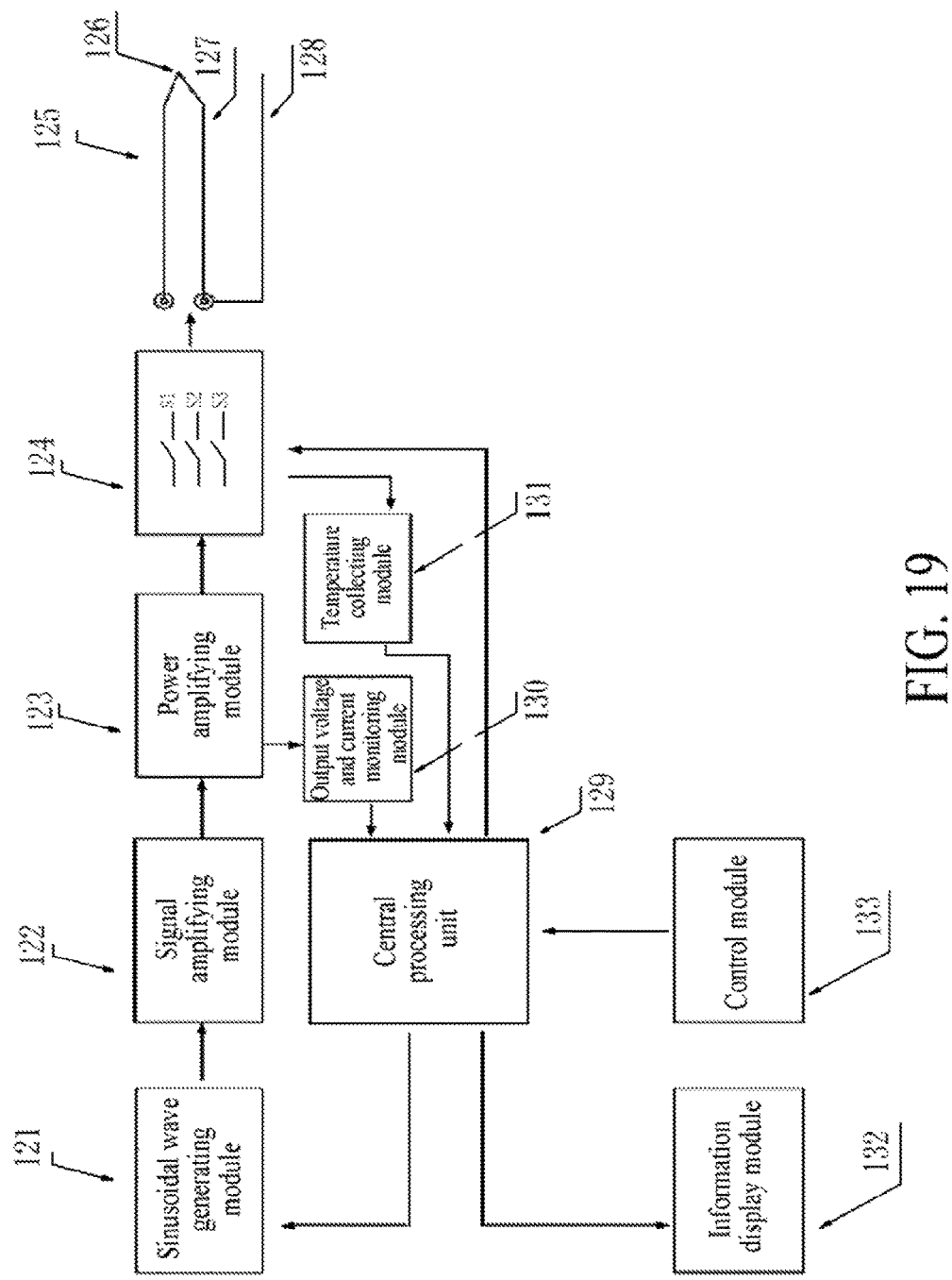
FIG. 19 is a working principle diagram of a complete machine of a radio frequency ablation instrument including a radio frequency electrode with both a temperature measuring function and an impedance measuring function.

As shown in FIG. 19, the temperature-controlling radio frequency instrument includes a sinusoidal wave generating module 121, a signal amplifying module 122, a power amplifying module 123, a switch module 124, a radio frequency electrode module, a central processing unit 129, an output voltage and current monitoring module 130, a temperature collecting module 131, an information display module 132, and a control module 133.

The central processing unit 129 is separately connected to the sinusoidal wave generating module 121, the information display module 132, and the control module 133; the radio frequency electrode module is connected to the central processing unit 129 via the switch module 124; the sinusoidal wave generating module 121, the signal amplifying module 122, the power amplifying module 123, and the switch module 124 are sequentially connected to the radio frequency electrode module. The output voltage and current monitoring module 130 is separately connected to the central processing unit 129 and the power amplifying module 123; and the temperature collecting module 131 is separately connected to the central processing unit 129 and the switch module 124.

In the temperature-controlling radio frequency instrument, the central processing unit 129 is used to control the switch module 124 to switch a working mode, and the central processing unit 129 is used to control the sinusoidal wave generating module 121 to generate different sinusoidal waves. The central processing unit 129 is further used to control data collecting actions of the output voltage and current monitoring module 130 and the temperature collecting module 131, and control the information display module 132 to display information. The information display module 132 is used to display radio frequency parameters and various monitoring results. The control module 133 includes multiple regulation keys, buttons, and corresponding circuits adapted to the control module 133, the control module 133 is connected to the central processing unit 129, and the parameters in a radio frequency ablation process may be regulated by regulating the control module 133.

The temperature-controlling radio frequency instrument has three working modes, the central processing unit 129 controls the switch module 124 to switch to one of the working modes, and the central processing unit 129 controls the sinusoidal wave generating module 121 to generate a sinusoidal wave in a corresponding frequency in the functional mode. The sinusoidal wave undergoes signal amplification by the signal amplifying module 122 and power amplification by the power amplifying module 123, passes through the switch module 124, and is finally transmitted to the radio frequency electrode module. When the switch module 124 is switched to an impedance measuring mode, the output voltage and current monitoring module 130 measures a current and a voltage output by the power amplifying module 123 and feeds back the current and the voltage to the central processing unit 129. When the switch module 129 is switched to a temperature measuring mode, the temperature collecting module 131 collects a current in a radio frequency loop, calculates the temperature, and feeds back the temperature to the central processing unit 129.

As shown in FIG. 19, in this embodiment, the switch module 124 includes three parallel-disposed switch components S1, S2, and S3, the radio frequency electrode module includes a radio frequency electrode 126, a thermocouple formed by the radio frequency electrode 126 and the second material, and a body surface electrode 128. The three switch components S1, S2, and S3 are respectively used for achieving connections with a radio frequency electrode wire 125, a thermocouple wire 127, and a wire connected to the body surface electrode 128. The radio frequency electrode wire 125 is also used as another thermocouple wire, and the radio frequency electrode wire 125 and the thermocouple wire 127 are respectively connected to the radio frequency electrode 126 and the second material connected to the radio frequency electrode 126. When the first switch S1 and the second switch S2 in the switch module 124 are closed, the radio frequency electrode 126 and the second material connected to the radio frequency electrode 126 form a thermocouple measuring loop. When the first switch S1 and the third switch S3 in the switch module 124 are closed, the radio frequency electrode 126 and the body surface electrode 128 form a radio frequency releasing loop. The radio frequency releasing loop is also used as an impedance measuring loop, and it can switch between the two working mode. In two working modes, the frequencies of the sinusoidal wave signal generated by the sinusoidal wave generating module 121 are different. For example, in a radio frequency ablation working mode, the frequency of the sinusoidal wave signal is 465 KHZ, and in an impedance measuring working mode, the frequency of the sinusoidal wave signal is 50 kHz or 100 kHz.

Figure 20:
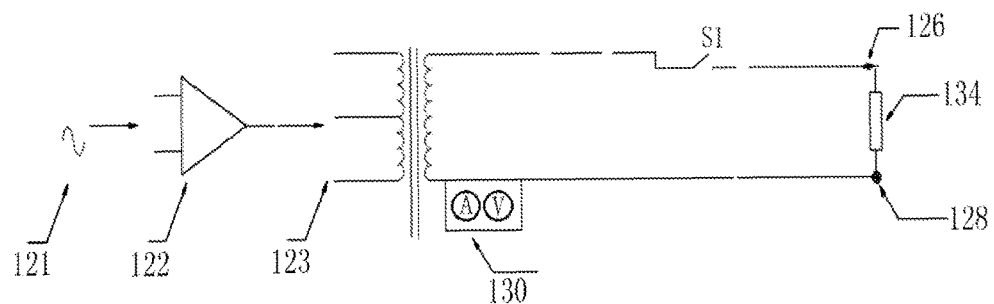
FIG. 20 is a schematic diagram of a working principle of impedance measuring.

In an impedance measuring working mode, as shown in FIG. 20, the sinusoidal wave generating module 121 generates a sinusoidal wave signal, and the sinusoidal wave signal undergoes signal amplification by the signal amplifying module 122 and power amplification by the power amplifying module 123, passes through the switch module 124, and then reaches the body impedance 134 via the radio frequency electrode wire 125 and the radio frequency electrode 126. In this case, the sinusoidal wave generating module 121 first generates a sinusoidal wave signal with a frequency of 50 khz and a power of 1 W, and the output voltage and current monitoring module 130 monitors changes of a voltage and a current without and with load to calculate impedance of a body loop; next, the sinusoidal wave generating module 121 outputs a sinusoidal wave signal with a frequency of 100 khz and a power of 1 W to perform measurement again; and finally, by using the body impedance obtained under two measuring frequencies, a median value is taken to obtain an impedance measuring result.

Figure 21:
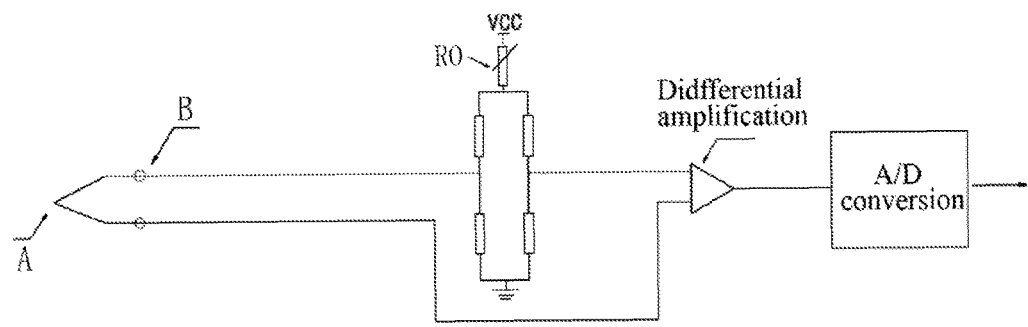
FIG. 21 is a principle diagram of temperature measuring of a temperature measuring loop including a cold end temperature compensating circuit.

In a temperature measuring working mode, the third switch S3 in the switch module 124 is open, the switches S1 and S2 are closed, the switches S1 and S2 are respectively connected to the radio frequency electrode wire 125 and the thermocouple wire 127, and the radio frequency electrode wire 125 is used as a thermocouple wire, so that the radio frequency electrode wire 125, the thermocouple wire 127, and the thermocouple formed by the second material and the radio frequency electrode form a loop. The temperature collecting module 131 collects a current change in the foregoing loop to calculate temperature of a thermocouple measuring point. As shown in FIG. 21, in a temperature measuring process, a contacting point, that is, a point A, formed by connecting two different materials is a hot end of the thermocouple, and a point B away from the radio frequency electrode is a cold end, and is also referred to as a reference end. When temperature of the point A changes, the thermocouple closed loop generates an electromotive force and an induced current. Because the environmental temperature changes, reference temperature is not absolute standard temperature. Therefore, as shown in FIG. 21, a bridge compensating circuit is connected in series at the cold end to perform compensation; and when environmental temperature changes, a resistance value of a thermistor RO also changes, so that the temperature change is in direct proportion to an electromotive force. In this case, when temperature of the hot end changes, a generated electromotive force is amplified by a differential amplifying circuit and undergoes A/D conversion to obtain a corresponding digital quantity for temperature display.

In a radio frequency releasing working mode, the radio frequency electrode has two radio frequency loading manners: one is the working mode used in the foregoing embodiment that a single radio frequency electrode and a body surface electrode form a loop, and the other is a working mode that double radio frequency electrodes form a loop. The two manners are separately described below with reference to FIG. 22a and FIG. 22b.

Figure 22A:
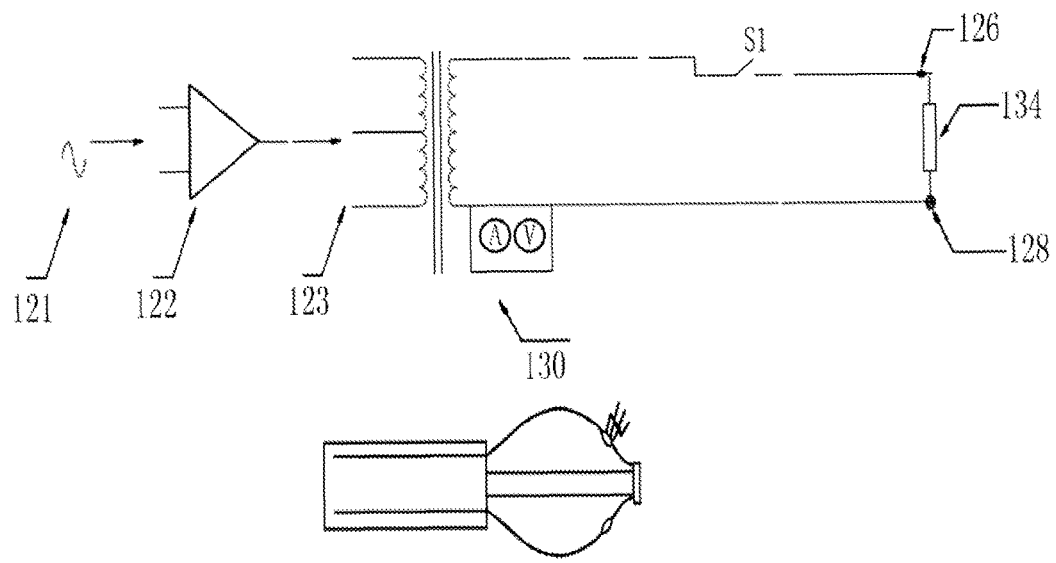
FIG. 22a is a schematic diagram of radio frequency releasing of a loop formed by a single radio frequency electrode and a body surface electrode.

Referring to FIG. 22a, each radio frequency electrode 126 and each body surface electrode 128 form a loop in manner 1. During radio frequency loading, a sinusoidal wave with a frequency of 465 KHZ generated by the sinusoidal wave generating module 121 passes through a power amplifying circuit, the switch S1 connection, signal is loaded on an electrode releasing point via a wire, and the radio frequency electrode 126 and the body surface electrode 128 form a loop via the body impedance 134. Released energy may be calculated by measuring output voltage and current values by using the output voltage and current monitoring module 130.

Figure 22B:
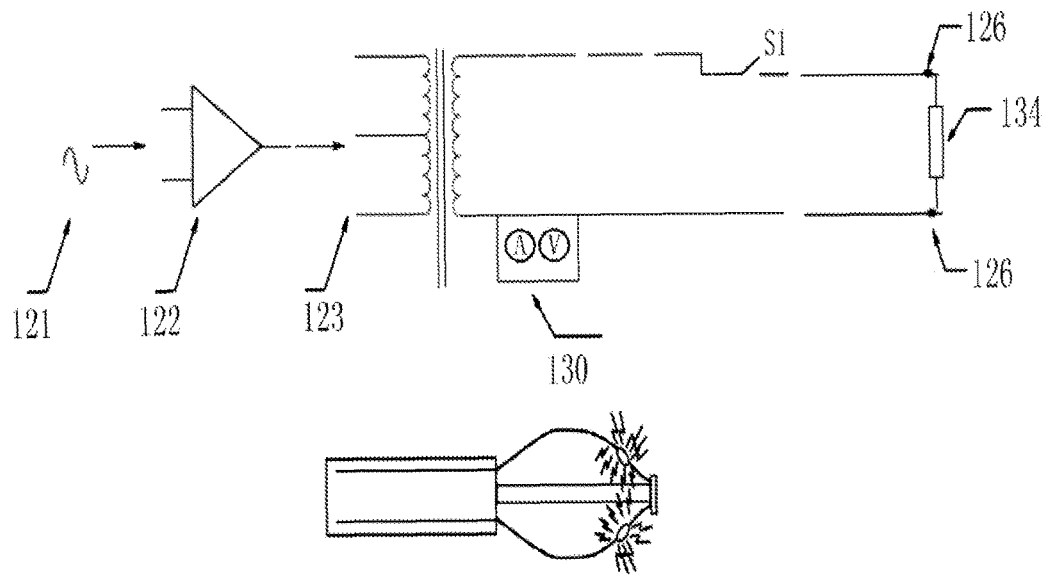
FIG. 22b is a schematic diagram of radio frequency releasing of a loop formed by double radio frequency electrodes.

Referring to FIG. 22b, every two radio frequency electrodes 128 form a loop in manner 2. During radio frequency loading, a sinusoidal wave with a frequency of 465 KHZ generated by the sinusoidal wave generating module 121 passes through a power amplifying circuit, and the switch S1 connection, signal is loaded on an electrode releasing point via a wire, and two radio frequency electrodes 126 form a complete loop via the body impedance 134. Released energy may be calculated by measuring output voltage and current values by using the output voltage and current monitoring module 130.

In conclusion, in the radio frequency electrode with both a temperature measuring function and an impedance measuring function provided by the present invention, a temperature measuring thermocouple is formed by connecting a second material to the radio frequency electrode to perform temperature measuring, and three functions: radio frequency releasing, temperature measuring, and impedance measuring may be implemented simultaneously in combination with a radio frequency releasing function and an impedance measuring function of a radio frequency releasing point. In a radio frequency system using the radio frequency electrode, a temperature sensor and an impedance sensor disposed near the radio frequency electrode in the prior art can be omitted, thereby improving the overall flexibility of the radio frequency electrode, and facilitating control of a radio frequency ablation process. In addition, the precision of temperature measuring and impedance measuring is improved by using the foregoing radio frequency electrode.

In the temperature-controlling radio frequency instrument provided by the present invention, by monitoring impedance of the radio frequency releasing point and monitoring temperature near the radio frequency releasing point, a quantitative feedback for a radio frequency ablation condition inside a lumen may be formed, to help a surgeon who executes a radio frequency ablation operation to master a radio frequency ablation process and regulate parameters.

Seventh Embodiment

Generally, a passage from in vitro to a heart or a renal artery needs to be established in an ablation tube under the assistance of a guide tube, and most of the ablation tube is left in the guide tube, that is, in ablation, the guide tube is wrapped around an outer wall of the ablation tube. Therefore, the inner diameter of the guide tube needs to be greater than the outer diameter of the ablation tube, so that the ablation tube can pass through the guide tube smoothly. In addition, during an operation, a DSA radiography device is needed to inject a radiocontrast agent into the guide tube, so that key information such as the shape, position, and size of a target part such as a vessel may be clearly observed. During an operation, physiological saline needs to be further injected into the guide tube to perform lavage, and heparin needs to be injected to perform anticoagulation. Therefore, under the premise of ensuring that the basic function and strength of an ablation tube are not affected, an interspace between the ablation tube and the guide tube needs to be further ensured, so as to fully meet requirements such as radiography, lavage, and anticoagulation.

In the prior art, the outer surface of the ablation tube is designed to be circular, the inner structure such as a wire is clad inside a circular pipe, and the interspace between the ablation tube and the guide tube can only be implemented by increasing the inner diameter of the guide tube, but the increase of the inner diameter of the guide tube definitely increases the difficulty of an ablation operation. In addition, to ensure that the ablation tube smoothly passes through the guide tube, an ablation tube with less resistance to the guide tube also needs to be provided.

Figure 23:
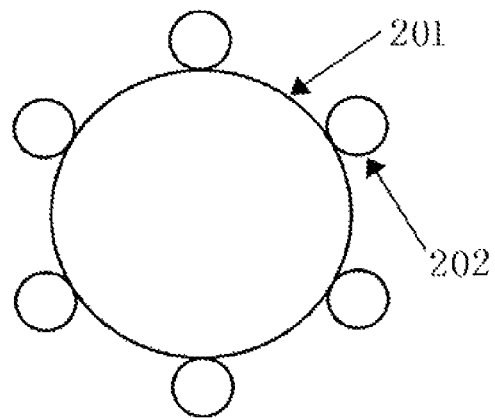
FIG. 23 is a schematic diagram of wire distribution of a radio frequency ablation tube with multiple grooves on the surface.
Figure 24A:
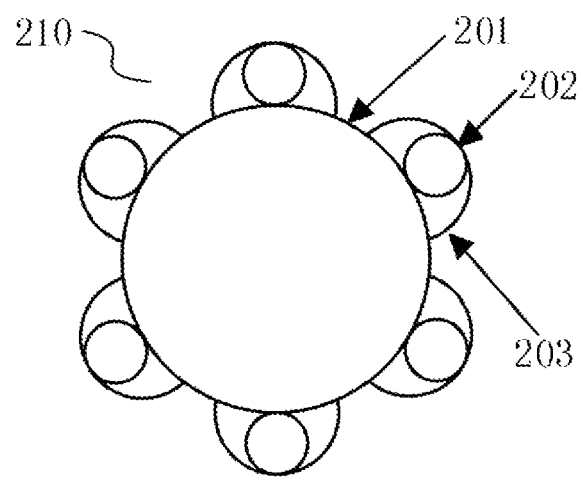
FIG. 24a is a schematic section diagram of the radio frequency ablation tube with multiple grooves on the surface in a seventh embodiment of the present invention.
Figure 24B:
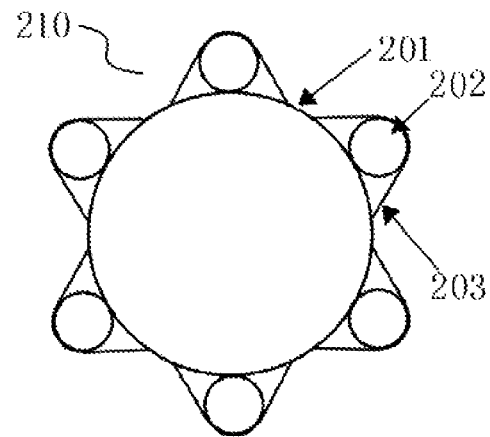
FIG. 24b is a schematic section diagram of the radio frequency ablation tube with multiple grooves on the surface in an eighth embodiment of the present invention.
Figure 25:
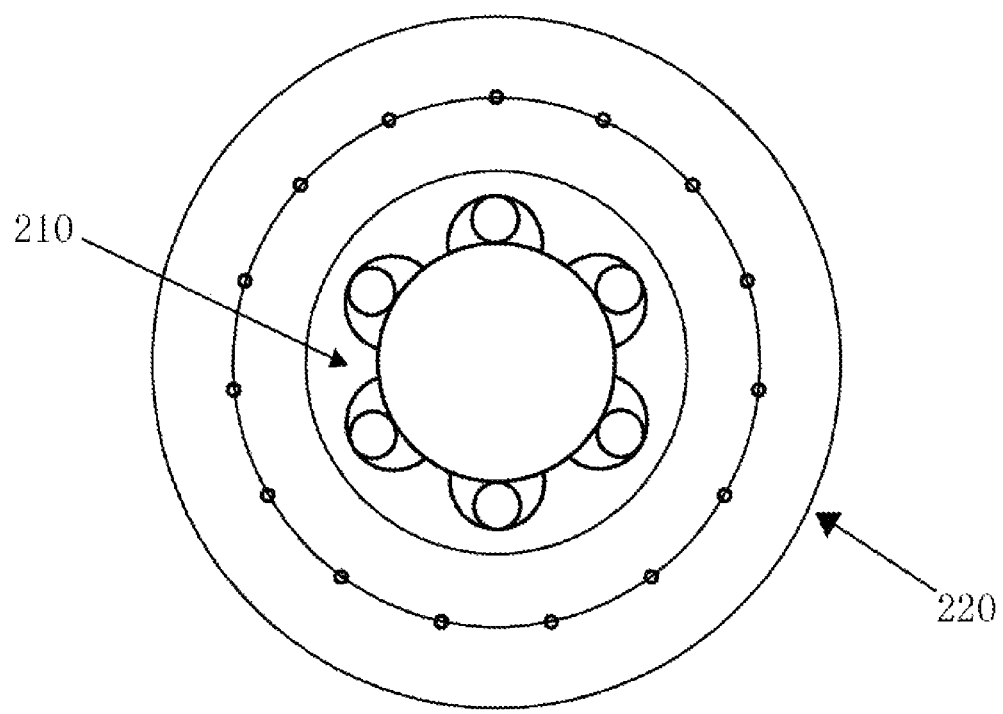
FIG. 25 is a schematic section diagram of a radio frequency ablation tube with multiple grooves on the surface in a guide tube.

With reference to FIG. 23 to FIG. 25, it can be known that an ablation tube 210 with multiple grooves on the surface (briefly referred to as an ablation tube 210 below) provided by the present invention includes a support tube 201 configured at the central part and multiple wires 202 configured on the outer surface of the support tube 201. The multiple wires 202 are configured around the circumferential direction of the support tube 201, and each wire 202 extends along the length direction of the support tube 201; a sealing layer 203 used for cladding the wire 202 is configured outside each wire 202, and each neighboring sealing layer 203 forms a groove on the outer surface of the support tube 201.

FIG. 24a shows the seventh embodiment of the present invention. Outside the circular support tube 201, six wires 202 are evenly configured along the outer circumferential direction of the support tube 201, and a 60° angle is formed by two connecting lines between the neighboring two wires 202 and the center of the support tube 201, so that the six wires 202 are arranged to be a plum blossom-form around the outer circumference of the support tube 201. In addition, a layer of plastic sealing layer 203 is disposed outside each wire 201 to form an ablation tube 210, and the cross-sectional shape of the ablation tube 210 also has a plum blossom-form. The cross section of the sealing layer 203 cladding the outside of a single wire 202 is arc-shaped, and the bottom of the sealing layer 203 is closely connected to the outer surface of the support tube 201, to form an arc-shaped space; and the wire 202 is configured in the arc-shaped space. In addition, each neighboring sealing layer 203 forms a groove on the outer surface of the support tube 201.

Eighth Embodiment

FIG. 24b shows the eighth embodiment of the present invention. In this embodiment, a configuration manner of wires 202 in the outer circumferential direction of a support tube 201 and the number of wires 202 are the same as those in the seventh embodiment. Its difference lies in a sealing layer 203 cladding the outside of a single wire 202 has a different cross-sectional shape. In the eighth embodiment, the cross section of the sealing layer 203 has an arc-shaped top, and a straight line side wall that is connected to the base line of the arc-shaped top and extends to the outer surface of the support tube 201. The arc-shaped top, the straight line side wall, and the outer surface of the support tube 201 form a closed space, and the wires 202 are separately configured in an independent closed space.

In the seventh embodiment and the eighth embodiment, the ablation tube 210 includes six wires 202, where sealing layers 203 outside the six wires 202 are independent of each other and do not touch each other. However, with the increase of the number of the wires 202, or with the increase of the touch area between the sealing layer 203 and the support tube 201, neighboring sealing layers 203 may also be connected together to cover the entire outer surface of the support tube 201. That is, the sealing layers 203 may be independent of each other, and may also be connected as a whole to form an integral sealing layer.

To ensure strength and tenacity of the ablation tube 210, the sealing layer 203 may be manufactured by using a polymer material, for example, any of polyurethane, polyethylene, polypropylene, and nylon. When the ablation tube 210 is manufactured, if the sealing layers 203 cladding the outside of different wires are connected as a whole, the sealing layers 203 may be manufactured by directly cladding a polymer material of equal thickness outside the wire 202.

The ablation tube 210 with multiple grooves on the surface provided by the present invention is characterized by a compact structure and a small volume. To further compress the volume of the ablation tube 210, the wire 202 may directly contact the outer surface of the support tube 201, and the wire 202 may also be tangent with the top of the sealing layer 203. That is, in the ablation tube 210, the wire 202 is tangent with the outer surface of the support tube 201, and the wire 202 is tangent with the top of the sealing layer 203.

As shown in FIG. 25, the ablation tube 210 with multiple grooves on the surface provided by the present invention needs to pass through the guide tube 220 during an ablation operation, and a passage from in vitro to a heart or a renal artery is established under the assistance of the guide tube 220. FIG. 25 also shows the structure of a guide tube 220 with an anti-electromagnetic interference function provided by the present invention, and specific content of disposing a shielding layer inside the guide tube 220 is introduced in detail in the tenth embodiment.

A use situation of the ablation tube 210 with multiple grooves on the surface provided by the present invention, and an interspace between the ablation tube 210 with multiple grooves on the surface and the guide tube 220 are introduced below with reference to FIG. 26a. In addition, the ablation tube 210 with multiple grooves on the surface provide by the present invention is compared with a generally used cylindrical ablation tube 210' in the prior art with reference to FIG. 26a and FIG. 26b.

In the prior art, the cylindrical ablation tube 210' clads the inner structure, such as a wire, inside a circular pipe, and the outer surface of the cylindrical ablation tube 210' is a smooth cylinder. As shown in FIG. 26b, when the cylindrical ablation tube 210' passes through the guide tube 220, the cylindrical outer surface may contact the inner surface of the guide tube 220, and the contact area is large. By comparison, as shown in FIG. 26a, when the ablation tube 210 with multiple grooves on the surface provided by the present invention passes through the guide tube 220, only the top of the sealing layer 203 may contact the inner surface of the guide tube 220, so that the contact area is substantially decreased, and frictional resistance is reduced, thereby facilitating an operation.

Figure 26A:
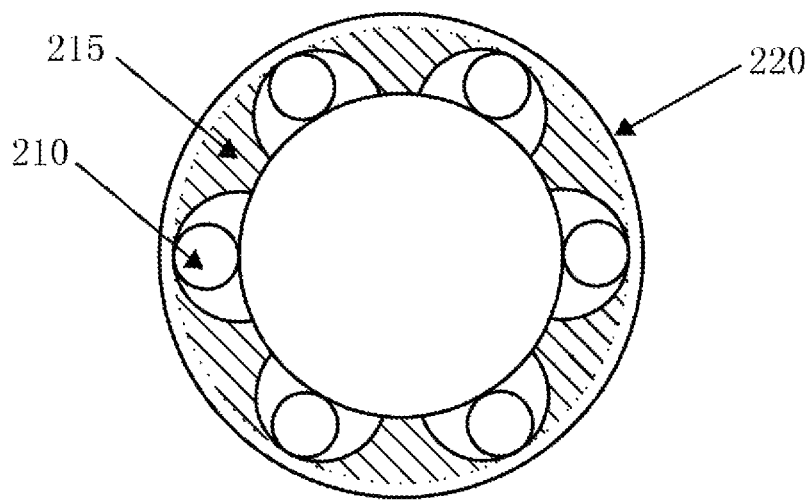
FIG. 26a is a schematic diagram of an interspace between the radio frequency ablation tube shown in FIG. 24a and a guide tube.
Figure 26B:
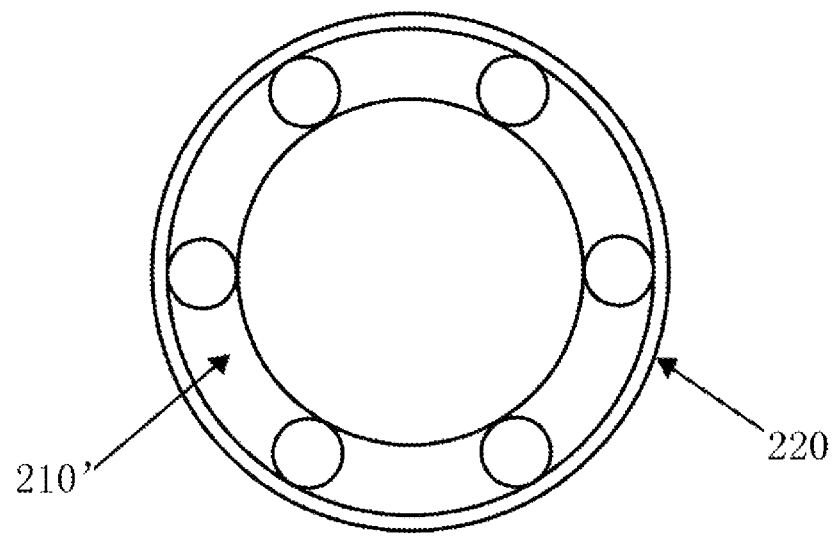
FIG. 26b is a schematic diagram of an interspace between an existing radio frequency ablation tube and a guide tube.

In addition, it can be known from the comparison of FIG. 26a and FIG. 26b that, inside the guide tubes 220 with a same tube diameter, the interspace between the ablation tube 210 with multiple grooves on the surface and the guide tube 220 is larger, and the grooves distributed on the outer surface of the ablation tube 210 may increase the interspace between the ablation tube 210' and the guide tube 220 in the prior art more than twice as large. By effectively using an interspace 215 between the ablation tube 210 with multiple grooves on the surface and an inner wall of the guide tube 220, requirements such as radiography, lavage, and anticoagulation may be fully met in an ablation operation. This interspace may contain more radiocontrast agents to enhance the radiography effect; larger lavage space may be obtained to improve the lavage effect of the guide tube; and more anticoagulation medicines such as heparin may be filled to exert an anticoagulation effect.

In conclusion, multiple wires are configured on the outer surface of the support tube of the ablation tube with multiple grooves on the surface provided by the present invention, and each wire is separately sealed via a different sealing layer, thereby forming multiple grooves on the outer surface of the ablation tube. Compared with the design in the prior art that the inner structure such as a wire is clad inside a circular pipe, the contact area between the outer surface of the ablation tube with multiple grooves on the surface and an inner wall of the guide tube is smaller, and frictional resistance is substantially reduced, thereby facilitating an operation. In addition, the interspace between the ablation tube with multiple grooves on the surface and the guide tube is larger, so that requirements such as radiography, lavage, and anticoagulation may be fully met in an ablation operation. The ablation tube with multiple grooves on the surface may also be applied in a heart or renal artery radio frequency ablation operation.

Ninth Embodiment

Because the radio frequency ablation operation is performed by directly intervening human vessels, the size of a radio frequency ablation tube needs to adapt to the diameter of human vessels. The diameter of a human renal artery is about between 2 mm and 10 mm, and in the prior art, the size of an electrode end of a radio frequency ablation tube is fixed, and therefore cannot adapt to diameters of different vessels of different human bodies. However, in some cases, there may also be a problem that electrodes cannot be adhered to a wall simultaneously. Therefore, radio frequency ablation tubes in different specifications need to be provided to meet requirements of different patients.

A renal artery ablation tube generally includes more than one group of electrodes, and each group of electrodes is connected to more than one wire to achieve the objectives of impedance measuring and radio frequency ablation. However, in the prior art, the manufacturing method of the radio frequency ablation tube generally is to first manufacture a wire and an electrode, and then assemble the wire, the electrode, and a tube body. Because the diameter of the tube is small and is between 1.5 mm and 2.5 mm, the wire diameter of the wire is between 0.1 mm and 0.5 mm, and the sizes have errors, the wire distribution inside the tube is quite complex, the uniformity of the wire distribution cannot be ensured, and the wires may interfere with each other when radio frequency discharging is performed. Therefore, the radio frequency ablation tube also needs to be improved.

A cable-type radio frequency ablation tube and a manufacturing method thereof provided by the present invention are described below with reference to the accompanying drawings and specific embodiments.

The cable-type radio frequency ablation tube provided by the present invention includes a control handle, a tube body, and an electrode section. The tube body is a cable-integrated tube body manufactured by using a cable manufacturing process, one end of the tube body is used for being connected to the control handle, and the other end of the tube body is used for manufacturing the electrode section. The center of the tube body is a penetrated through hole, and a telescopic control wire passes through the through hole, with one end connected to the control handle, and one end fixed together with the distal end (that is, the front) of the electrode section.

In the cable-type radio frequency ablation tube, the tube body includes multiple groups of memory alloy wires and metal wires that are covered by a cable cladding layer and insulated from each other, one end of the memory alloy wire is used for manufacturing a memory alloy support, the middle section of the memory alloy support is exposed to form a conductive section, the metal wire is wound around the conductive section, and an electrode material is fixed on the wound metal wire to form an electrode section.

The memory alloy and the metal wire that form the memory alloy support form a thermocouple, to measure temperature of a radio frequency releasing point. The memory alloy wire may use any one of a nickel-titanium alloy, a copper-nickel alloy, and a titanium alloy, and may also use another memory alloy material; the material of the metal wire is any one of pure copper, a copper-zinc alloy, a platinum alloy, and a nickel-chromium alloy, and the electrode material is platinum and another electrode material.

The tube body of the cable-type radio frequency ablation tube is obtained via a cable manufacturing process, so that the multiple internal wires may be orderly arranged, and insulation from each other may be ensured. The radio frequency electrode support is formed by four to eight petal-shaped supports, and the material of the radio frequency electrode support is a memory alloy, which may deform under the effect of an external force, and restore the shape before deformation immediately after the external force disappears. To ensure an electrode to be adhered to a wall desirably, after the petal-shaped support is contracted into an arched shape inside a vessel, a control handle may be used for extending a telescopic control wire to control the diameter of the electrode section, to make the electrode section adapt to different diameters of renal arteries of different patients.

A manufacturing method of the cable-type radio frequency ablation tube is described below by using a radio frequency electrode support formed by a nickel-titanium alloy as an example.

First, embed an enamel-covered copper wire 301 and an enamel-covered nickel-titanium alloy wire 302 at a cable cladding layer, and draw a tube body to shape in a cable-drawing manner.

Next, peel off the cable cladding layer at the two ends of the tube body, with one end used for being connected to the control handle, and one end manufactured into an electrode section. A step of manufacturing an electrode section by using one end of the tube body is described below with reference to FIG. 1 to FIG. 7.

Figure 27A:
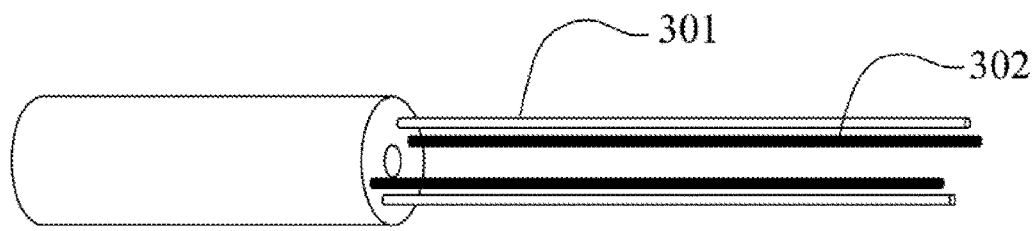
FIG. 27a is a schematic diagram of a nickel-titanium wire and a copper wire of a tube body of a radio frequency ablation tube exposed, after a cable cladding layer close to an electrode end of the tube body of the radio frequency ablation tube is peeled off, when a cable-type radio frequency ablation tube is manufactured in a ninth embodiment of the present invention.

(1) As shown in FIG. 27a, after a tube body is manufactured, peel off a cable cladding layer close to an electrode end of the tube body to expose a copper wire 301 and a nickel-titanium alloy wire 302 inside the tube body.

Figure 27B:
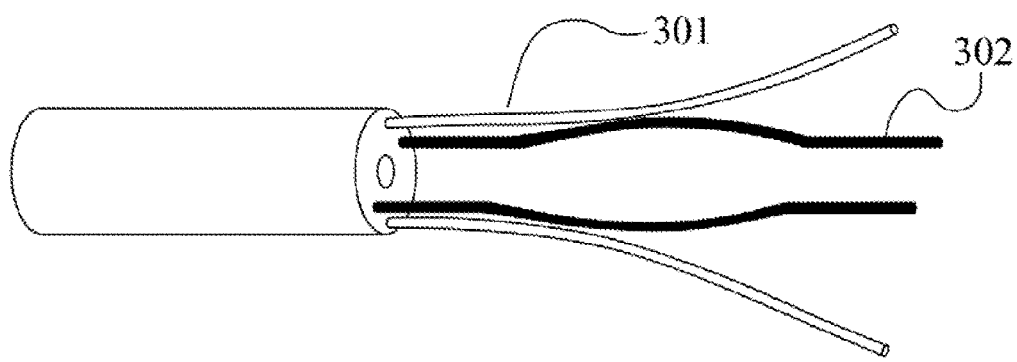
FIG. 27b is a schematic diagram of an electrode support manufactured, after an insulating layer of the exposed nickel-titanium wire in FIG. 27a is peeled off.

(2) As shown in FIG. 27b, peel off an insulating layer of the exposed nickel-titanium wire 302, and shape the nickel-titanium alloy wire as a shape of an electrode support by using a shaping fixture, to form a memory alloy support.

Figure 27C:
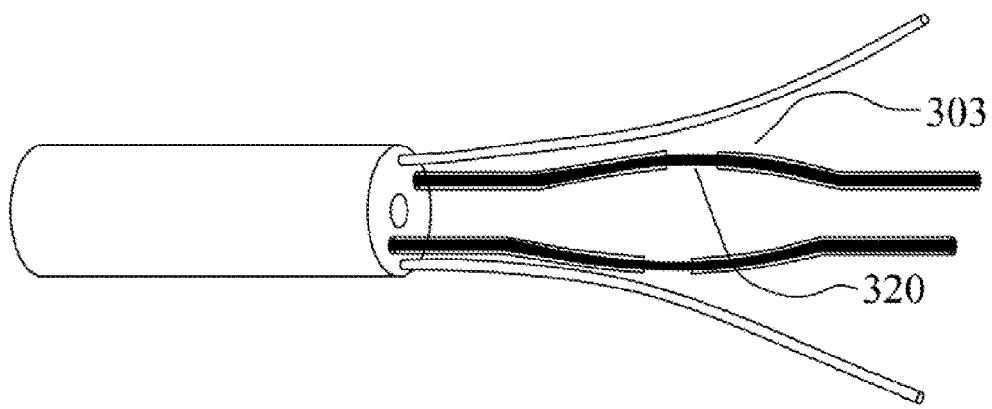
FIG. 27c is a schematic diagram of a conductive section formed, after the near end and the distal end of the nickel-titanium wire with the insulating layer peeled off in FIG. 27b are separately sleeved with a heat contraction tube for insulation, and the middle section is exposed.

(3) As shown in FIG. 27c, separately sleeve the near end and the distal end of the nickel-titanium alloy support with a heat contraction tube for insulation, so that the middle section is exposed as a conductive section 303.

Figure 27D:
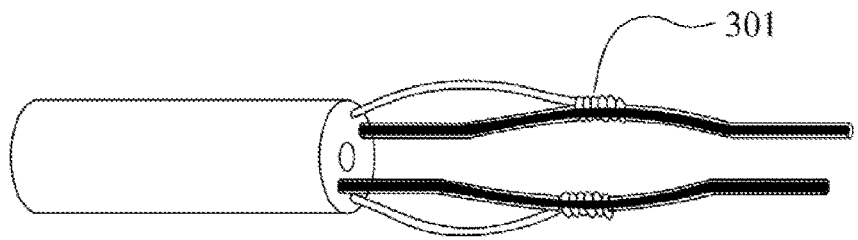
FIG. 27d is a schematic diagram of a thermocouple formed by winding the exposed copper wire in FIG. 27a around the exposed section of the nickel-titanium wire.

(4) As shown in FIG. 27d, peel off an insulating layer of the copper wire 301, and wind the copper wire 301 around the exposed section of the nickel-titanium alloy support (that is, the conductive section 303) to form a thermocouple.

Figure 27E:
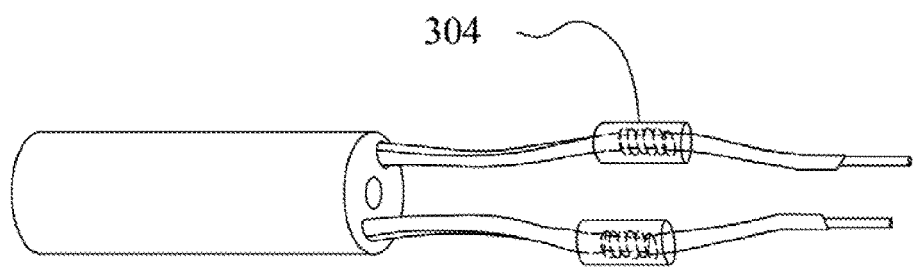
FIG. 27e is a schematic diagram of an electrode section formed by sleeving a platinum ring on the wound copper wire in FIG. 27d.

(5) As shown in FIG. 27e, sleeve a platinum ring 304 on the wound copper wire to be fixed, where soldering may be used or bonding with glue may be used, and seal the two ends of the platinum ring by glue.

Figure 27F:
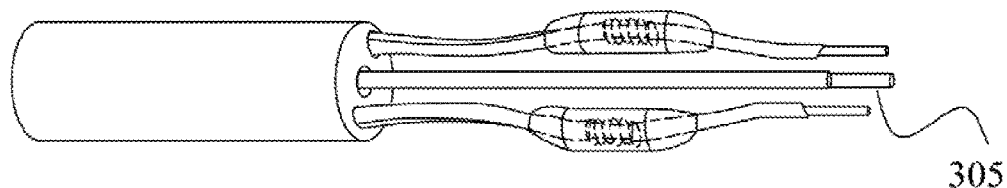
FIG. 27f is a schematic diagram of penetrating a telescopic control wire from a central hole of a tube body of a radio frequency ablation tube.

(6) As shown in FIG. 27f, after the platinum electrode 304 is fixed on the nickel-titanium alloy support, placing the telescopic control wire 305 from a central hole at the center of the tube body.

Figure 27G:
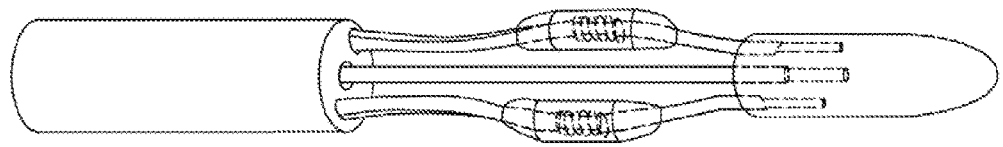
FIG. 27g is a schematic diagram of fixing the distal end of the nickel-titanium support and the distal end of the telescopic control wire together.

(7) As shown in FIG. 27g, fix the distal end of the nickel-titanium alloy support and the distal end of the telescopic control wire 305 together, where glue sealing or another manner may be used for fixing.

The manufacturing method of the cable-type radio frequency ablation tube provided by the present invention is described above, where the tube body is manufactured in a cable-integrated manner. First, the tube body is manufactured and then an electrode section part is processed. The manufacturing process is mature, and the process is simple and easy to control. In the tube body, a total of 8 to 18 groups of wires are distributed, and impedance measuring, temperature measuring, and radio frequency discharging are independently completed between the electrodes. All groups of wires are insulated from each other, and do not interfere with each other during discharging.

Compared with a manufacturing method in the prior art that a wire and an electrode are manufactured first, and then the wire, the electrode and a tube body are assembled, the cable-type manufacturing process can ensure that wires in the tube body are orderly arranged, and are insulated from each other, thereby avoiding uneven arrangement of wires during assembling, and also avoiding mutual interference of the wires.

The cable-type radio frequency ablation tube further includes a temperature measuring section. The temperature measuring section is a thermocouple formed by a copper wire and a nickel-titanium alloy wire, where the copper wire is also a radio frequency discharging wire and an impedance measuring wire, and temperature measuring, impedance measuring, and radio frequency discharging are performed intermittently. Experiments have proven that the thermocouple formed by a copper wire and a nickel-titanium wire is well matched, and temperature of tissue may be accurately measured in a working temperature range.

In the foregoing embodiment, the radio frequency electrode support is formed by a nickel-titanium alloy, and because the nickel-titanium alloy is a memory alloy, when the radio frequency electrode support is at proper temperature, the radio frequency electrode support may restore an original fixed shape, for example, restore an arched shape in a body temperature condition, thereby implementing contact and attachment between the radio frequency electrode and a target vessel. The radio frequency electrode may also be formed by using another memory alloy such as a copper-nickel alloy or a titanium alloy. In addition, when the nickel-titanium alloy cannot be adhered to a wall completely according to its own deformation, the telescopic control wire may be used for deforming the radio frequency electrode support to perform further control, to adhere the nickel-titanium alloy to a wall completely.

Tenth Embodiment

In a radio frequency ablation operation, especially in a renal artery nerve ablation operation, a heart cardiac ablation operation, and a nerve interventional operation, electrophysiological monitoring needs to be performed on tissue of a heart or renal artery ablation area, and nerve tissue, before an operation, during an operation, and after an operation.

Because an electrophysiological signal is quite weak, and the difference is also quite slight, if the electrophysiological signal is interfered by a signal in an environment electric field and magnetic field, a detecting instrument cannot monitor these slight changes and fluctuations. Therefore, an anti-interference capability of a monitoring system is important guarantee for the accuracy and sensitivity of a monitoring result.

When a heart and renal artery nerve ablation operation is performed, because a long ablation tube is needed in the operation, during working, the ablation tube must enter a heart or a renal artery from in vitro along a vessel passage, and the line for performing monitoring is also long. Therefore, the degree of interference is also increasingly obvious.

In a general case, a shielding mesh is designed on an outer layer wall of the ablation tube, to reduce interference of an environmental electromagnetic wave on detection of an electrophysiological signal. However, this method may increase the overall size of the ablation tube, the expansion of the outer diameter of the ablation tube may increase damage for a patient, and the ablation operation cannot be implemented for a patient with small vessels.

During working, a passage from in vitro to a heart or a renal artery needs to be established in the ablation tube under the assistance of a guide tube, and most of the ablation tube is left in the guide tube, that is, in ablation, the guide tube is wrapped around an outer wall of the ablation tube. Therefore, the guide tube with an anti-electromagnetic interference function mentioned in the seventh and eighth embodiments will be introduced in detail in the tenth embodiment. By means of a tube body disposed on the guide tube and a shielding mesh in the rear interface, interference of an external electromagnetic wave on the ablation tube can be eliminated or remarkably reduced, and the outer diameter of the ablation tube can be reduced, so that pain of a patient can be relieved, thereby also providing great guarantee for accuracy of a monitoring result.

Figure 28:
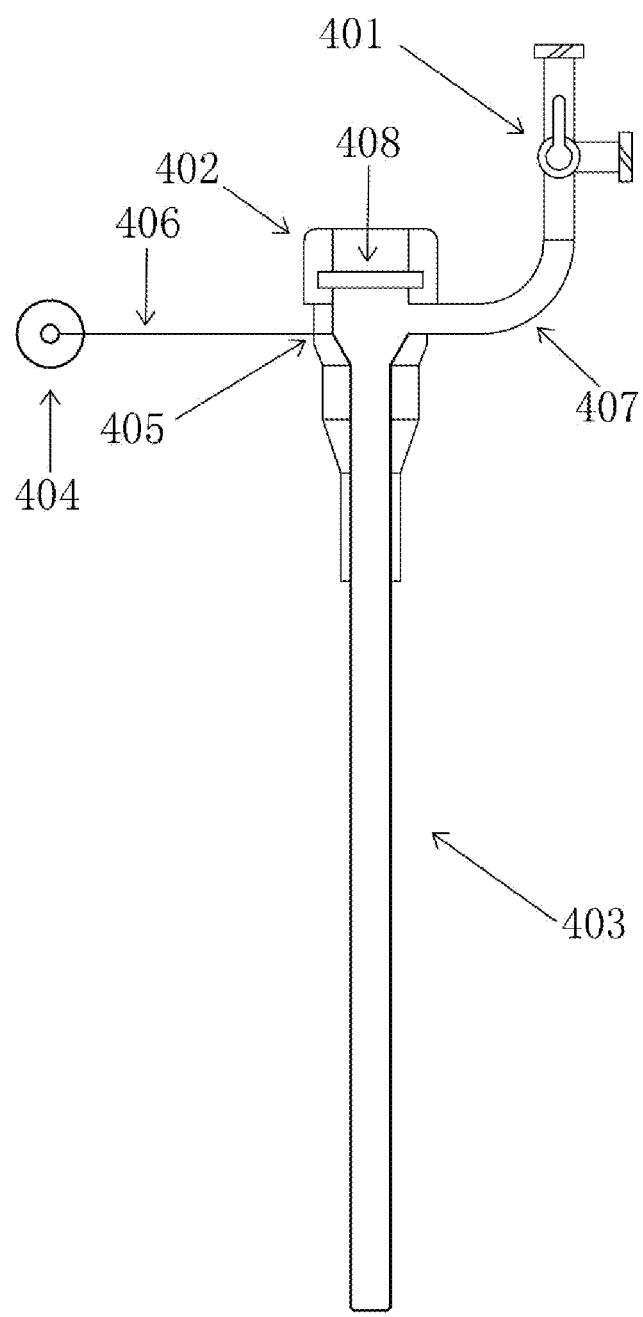
FIG. 28 is a schematic structural diagram of a guide tube with an anti-electromagnetic interference function in a tenth embodiment of the present invention.

As shown in FIG. 28, the guide tube with an anti-electromagnetic interference function provided by the present invention includes a cylindrical hollow tube body 403. A port is disposed at the front of the tube body 403, a rear interface 402 is disposed at the rear of the tube body 403, and the rear of the tube body 403 refers to an end that is of the tube body 403 and away from a patient body, where the rear interface 402 is connected to a three-way valve 401 via a tube 407, a hemostasis valve 408 is disposed inside the rear interface 402, and the rear interface 402 is connected to a skin electrode 404 via a wire 406. In addition, a shielding mesh 412 woven by a conductive material is disposed in the tube body 403 and the rear interface 402 of the guide tube, the conductive material is woven crosswise along a tube wall of the tube body 403 to form a closed annular shielding mesh, and the shielding mesh 412 is led out at the rear interface 402 to form a joint 405, where the joint 405 is grounded.

Figure 29A:
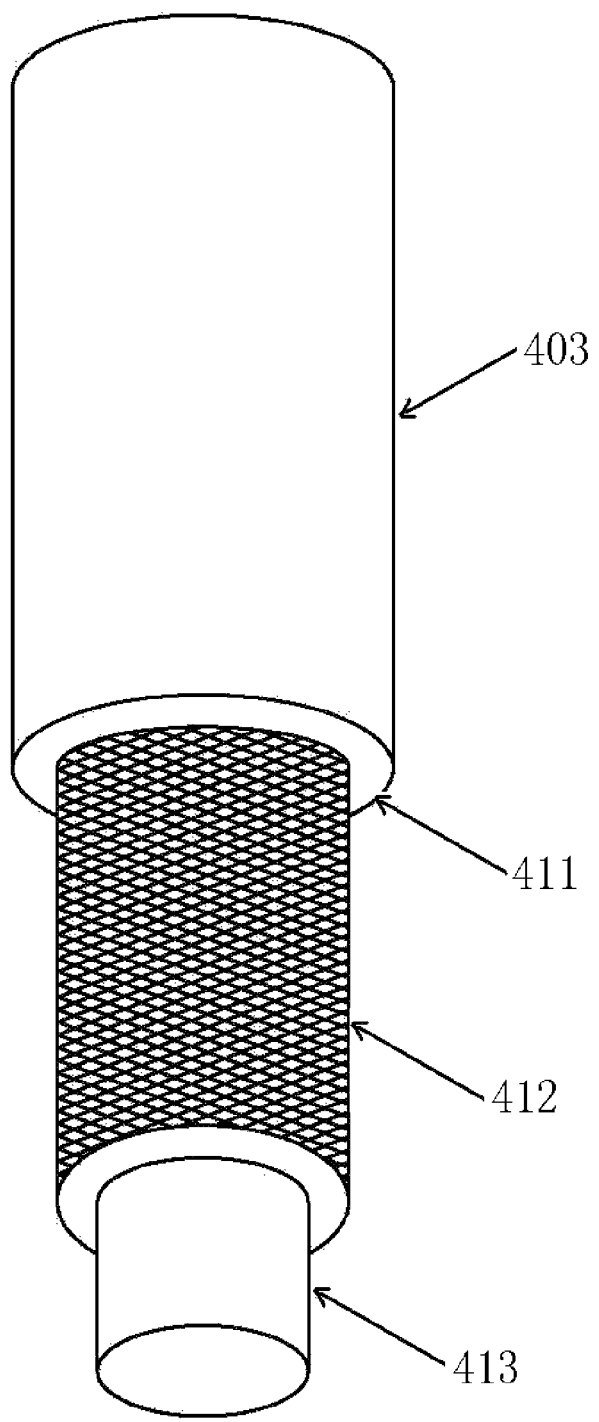
FIG. 29a is a schematic sectional view of the guide tube shown in FIG. 28.
Figure 29B:
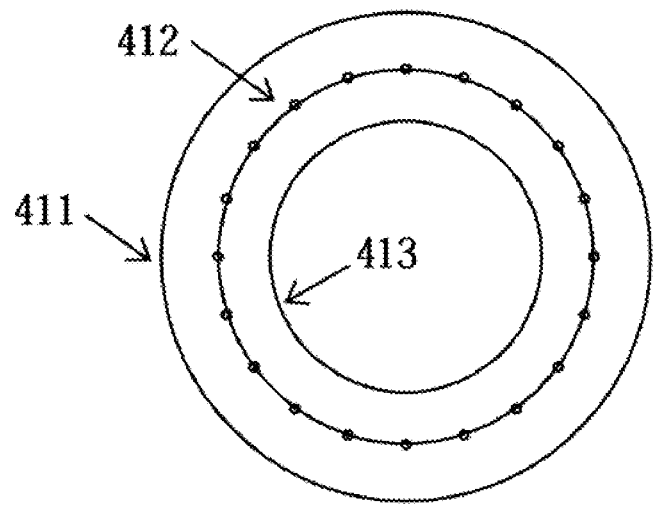
FIG. 29b is a schematic section diagram of the guide tube shown in FIG. 28.
Figure 29C:
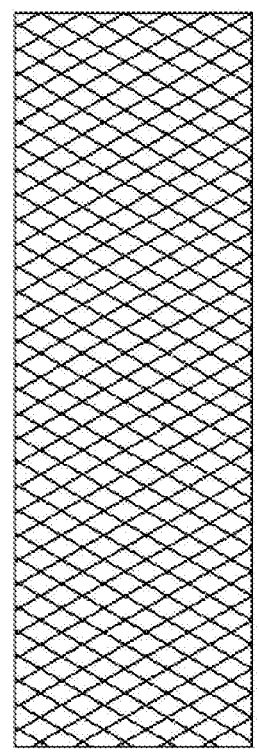
FIG. 29c is a schematic diagram of an expanded shielding mesh in the guide tube shown in FIG. 28.

With reference to FIG. 28 to FIG. 29c, it can be known that to ensure safety of the guide tube and prevent the shielding mesh 412 from being damaged in a use process, the shielding mesh 412 is disposed as a middle layer of the tube body 403, and the shielding mesh 412 separates the tube body 403 into a tube inner layer 413 and a tube outer layer 411. Referring to FIG. 29a, it can be known that the shielding mesh 412 is woven by a conductive material, and the conductive material is woven crosswise along a tube wall of the tube body 403 to form a closed annular shielding mesh 412. From a diagram of an expanded shielding mesh shown in FIG. 29c, it can be known that after the shielding mesh 412 is expanded, horizontal lines and vertical lines are woven in a certain angle. When the shielding mesh 412 is disposed in the tube body 403, the horizontal lines are obliquely wound around the tube inner layer 413, the vertical lines and the horizontal lines are obliquely wound around the tube inner layer 413 in the opposite direction, and the horizontal lines and the vertical lines are constantly crossed and woven around the outside of the tube inner layer 413 to form an annular shielding mesh. The shielding mesh is woven by a conductive material, and the conductive material may be selected from conductive materials such as a stainless steel material, a nickel-titanium material, and carbon fiber. The weaving density of the shielding mesh may be different, for example, may be selected between 30 pic and 200 pic, where pic represents the number of crossing points per inch of a woven mesh.

Figure 30:
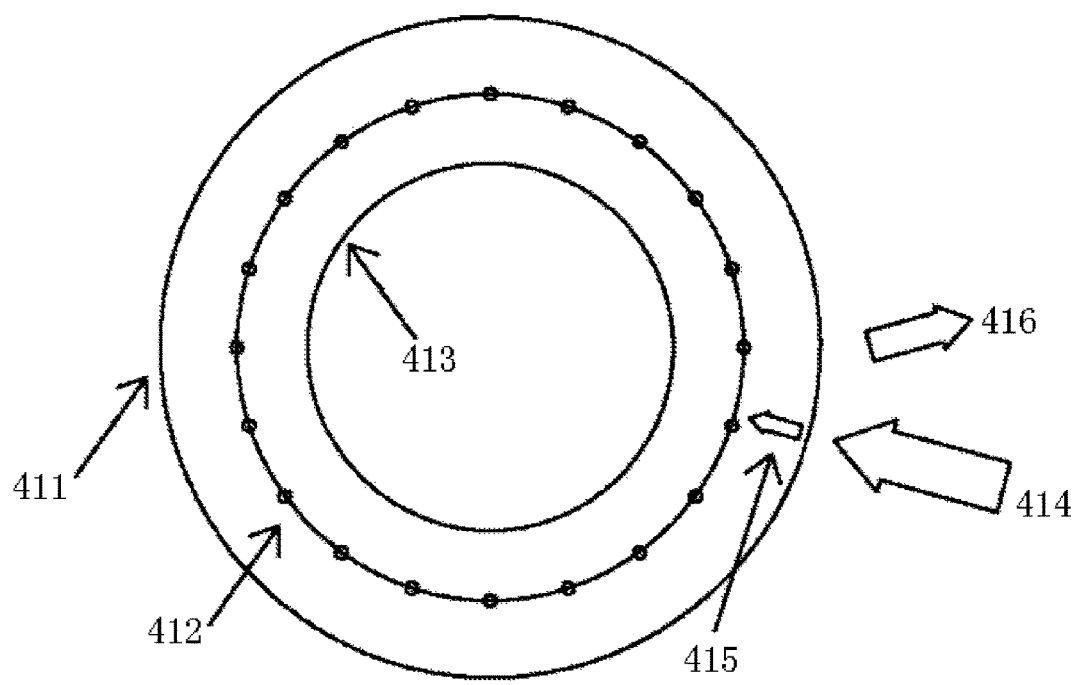
FIG. 30 is a schematic diagram of an electromagnetic shielding principle of the guide tube shown in FIG. 28.

Referring to a diagram of an electromagnetic shielding principle shown in FIG. 30, the conductive material is woven crosswise along a tube wall of the tube body 403 to form a closed annular shielding mesh. When electromagnetic interference 414 radiates to the guide tube 403, the electromagnetic interference 414 passes through the tube outer layer 411 to reach the shielding mesh 412. Only a small number of electromagnetic waves 415 may pass through the shielding mesh 412 and be absorbed, and most of the electromagnetic waves 416 are reflected, thereby greatly reducing electromagnetic interference of an environmental electromagnetic field on an ablation tube disposed inside the guide tube.

The disposing manner and the shielding principle of the shielding mesh 412 in the guide tube are introduced above, and a grounding manner of the shielding mesh 412 is illustrated below with reference to FIG. 31 to FIG. 33.

Figure 31:
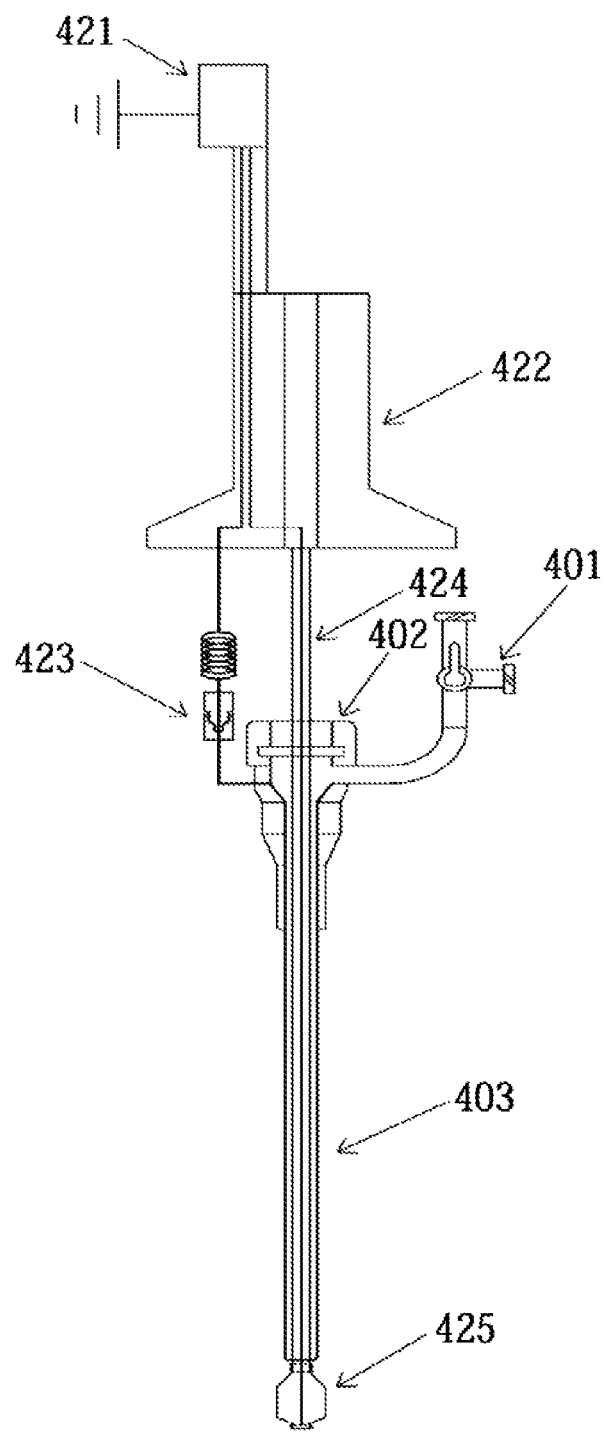
FIG. 31 is a schematic diagram in which a shielding mesh is grounded via an integrated cable.

FIG. 31 is a schematic diagram in which a guide tube and an ablation tube are used in combination. A ablation tube 424 enters the inside of a guide tube 403 via a rear interface 402, a radio frequency electrode 425 of the ablation tube 424 threads out from a port of the front of the guide tube 403 and acts on human body; the rear of the ablation tube 424 is connected to the control handle 422; a strip-shaped connecting electrode is disposed inside the ablation tube 424, the front of the strip-shaped connecting electrode extends to the radio frequency electrode 425, and the rear passes through the control handle 422 to be connected to an integrated cable joint 421.

In the guide tube provided by the present invention, a shielding mesh 412 may be grounded in different manners. For example, as shown in FIG. 31, a joint 405 of the shielding mesh 412 is disposed as a plug joint 423, and the shielding mesh 412 is connected to an integrated cable via the plug joint 423; and the integrated cable passes through the control handle 422 to reach the integrated cable joint 421 and is grounded. Alternatively, as shown in FIG. 32, the shielding mesh 412 may be grounded via a skin electrode 404 connected to the rear interface 402, where the joint 405 is connected to the skin electrode 404, and the skin electrode 404 is grounded. Or, as shown in FIG. 33, the joint 405 of the shielding mesh 412 may be directly grounded via a lead wire.

In the foregoing embodiment, a hemostasis valve 408 is disposed in the rear interface 402 of the guide tube, but a structure that no hemostasis valve disposed in the rear interface 402 is not excluded. For example, as shown in FIG. 34, in a guide tube without a hemostasis valve, a shielding mesh woven by a conductive material may also be disposed in the tube body 403 and the rear interface 402, and the shielding mesh is led out at the rear interface 402 to form a joint 405, where the joint 405 may be directly grounded as shown in FIG. 34, and may also be grounded via the skin electrode 404 connected to the joint 405 or an integrated cable.

Figure 32:
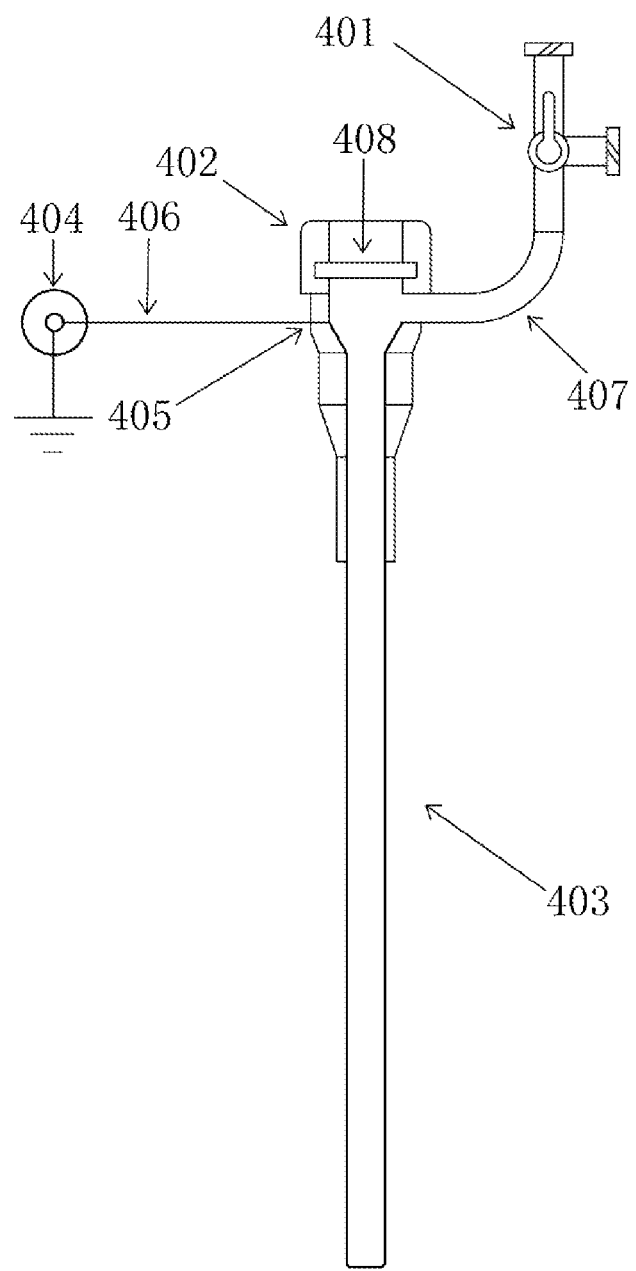
FIG. 32 is a schematic diagram in which a shielding mesh is grounded via a skin electrode.
Figure 33:
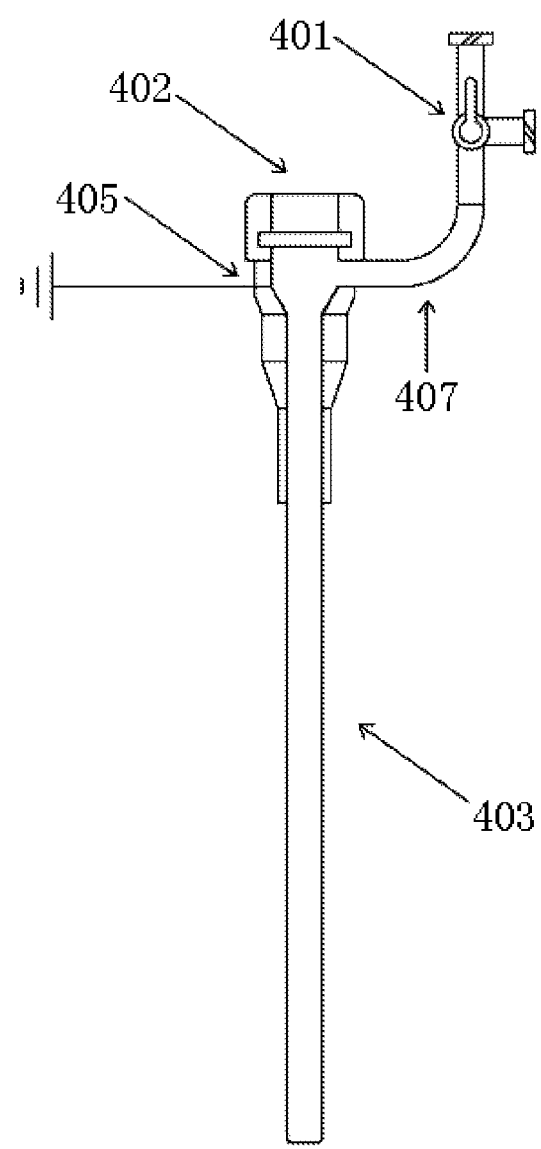
FIG. 33 is a schematic diagram in which a shielding mesh is directly grounded via a lead wire.

In the embodiment shown in FIG. 31 to FIG. 33, a hemostasis valve 408 is disposed inside a rear interface 402 of a guide tube, and the rear interface 402 is connected to a three-way valve 401 via a tube 407. To meet requirements such as radiography, lavage, and anticoagulation in an ablation operation, a radiocontrast agent may be injected into a tube body 403 of a guide tube to perform radiography, physiological saline may be injected to perform lavage, and heparin may be injected to perform anticoagulation via the three-way valve 401.

Figure 34:
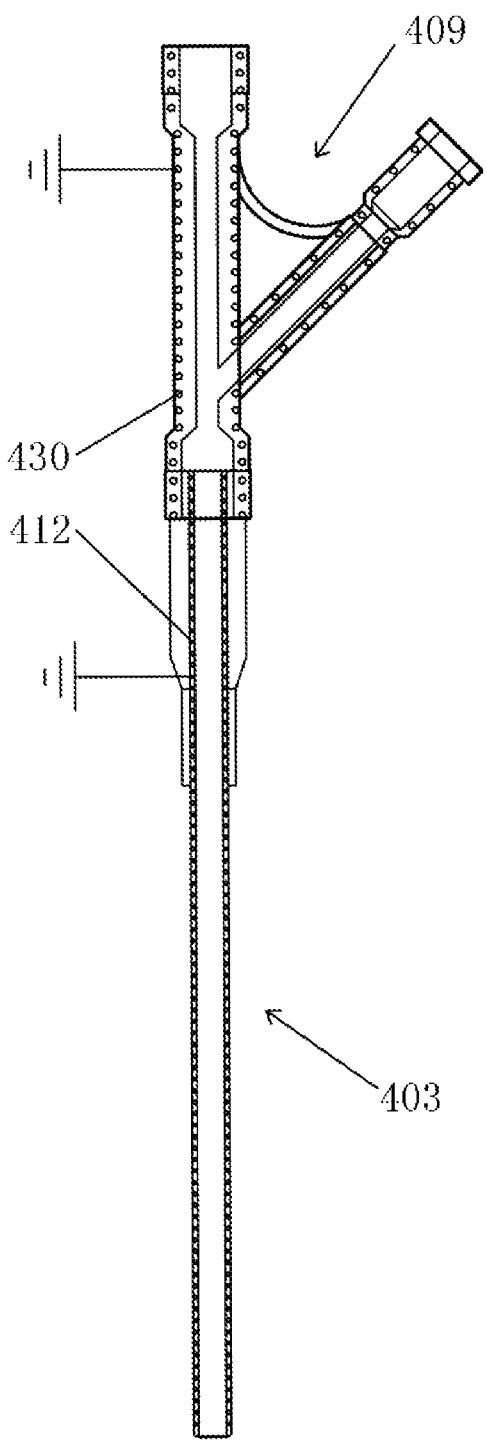
FIG. 34 is a schematic structural diagram of a shielding mesh of a guide tube that does not include a hemostasis valve and has an anti-electromagnetic interference function.

In the embodiment shown in FIG. 34, no hemostasis valve is disposed inside the rear interface 402 of the guide tube, and the rear interface 402 is also not connected to the three-way valve. To make it convenient to inject a radiocontrast agent into the tube body 403 of the guide tube to perform radiography, inject physiological saline to perform lavage, and inject heparin to perform anticoagulation, the rear interface 402 of the guide tube may be connected to a Y-shape valve 409, and the Y-shape valve 409 may be in a bolt connection to the rear interface 403, to implement a sealing effect. Meanwhile, to ensure an anti-electromagnetic interference function of the guide tube, a shielding mesh 430 woven by a conductive material is also disposed inside a tube body of the Y-shape valve 409, and the shielding mesh 430 is grounded via a lead-out joint.

It can be known from the foregoing that, in the guide tube with an anti-electromagnetic interference function provided by the tenth embodiment, a shielding mesh with an anti-electromagnetic interference function is designed in a tube body, which has an electromagnetic shielding effect on an inner ablation tube, thereby reducing or eliminating interference of environmental electromagnetic waves on the ablation tube. In an ablation operation in which the guide tube is applied to a heart and a renal artery, the effect of an environmental electromagnetic field on an ablation tube monitored signal can be counteracted, thereby improving accuracy and sensitivity in measuring an electrophysiological signal. In addition, while the tube body of the guide tube is effectively used, the size of a radio frequency ablation tube is reduced, and mesh structure of a mesh-form shielding may also enhance the strength of the tube body of the guide tube.

In conclusion, the radio frequency ablation method and system, and the radio frequency ablation device thereof provided by the present invention are introduced above. In the radio frequency ablation method, an ablation process is monitored by using guiding parameters and by using a temperature detecting module and an impedance measuring module, so that radio frequency ablation is safe and controllable. Meanwhile, in the present invention, by improving a radio frequency electrode, a radio frequency ablation tube, and a guide tube in the radio frequency ablation device, the precision of a radio frequency ablation operation is higher, damage to vessels of a patient is less severe, and complications are reduced.

The radio frequency ablation method and system, and the radio frequency ablation device thereof provided by the present invention are described in detail above. Any obvious modification made by a person skilled in the art without departing from the essence and spirit of the present invention shall constitute infringement of patent right of the present invention, and must undertake corresponding legal responsibility.

What is claimed is:

1. A radio frequency ablation device, comprising:
   a radio frequency ablation tube, a control handle, and a temperature-controlling radio frequency instrument, wherein the middle section of the radio frequency ablation tube carries a strip-shaped connecting electrode, a radio frequency electrode is formed at the distal end of the radio frequency ablation tube, and the radio frequency electrode is connected to the control handle via the strip-shaped connecting electrode;

the control handle comprises a tube guiding control handle for controlling the degree of curvature of the distal end of the radio frequency ablation tube, and a tube electrode control handle and a tube electrode auxiliary control handle for controlling the degree of opening of the radio frequency electrode;

an integrated interface is disposed at the rear of the control handle, and the temperature-controlling radio frequency instrument is connected, via an integrated cable, to the integrated interface disposed on the control handle; and a tube body of the radio frequency ablation tube is a cable-integrated tube body manufactured by a cable manufacturing process, the tube body comprises multiple groups of memory alloy wires and metal wires that are insulated from each other, one end of the memory alloy wire is used for manufacturing a memory alloy support, the middle section of the memory alloy support is exposed to form a conductive section, the metal wire is wound around the conductive section, and an electrode material is fixed on the wound metal wire to form an electrode section.

2. The radio frequency ablation device according to claim 1, wherein:
a multiplex channel is disposed at the central position of the integrated interface, and an impedance electrode interface, a temperature-controlling electrode interface, and a radio frequency electrode interface are separately disposed outside the multiplex channel.

3. The radio frequency ablation device according to claim 1, comprising:
a guide tube disposed outside the radio frequency ablation tube, wherein the guide tube has an anti-electromagnetic interference function, wherein
the guide tube comprises a cylindrical hollow tube body, wherein a port is disposed at the front of the tube body, a rear interface is disposed at the rear of the tube body, the tube body and the rear interface comprise a shielding mesh woven by a conductive material, the conductive material is woven crosswise along a tube wall of the tube body to form a closed annular shielding mesh, and the shielding mesh is led out at the rear interface to form a joint, wherein the joint is grounded.

4. The radio frequency ablation device according to claim 1, wherein:
the radio frequency electrode has both a temperature measuring function and an impedance measuring function;
the radio frequency electrode comprises a radio frequency releasing point, wherein the radio frequency releasing point is also used as an impedance measuring point; and
a second material is connected to the radio frequency electrode for forming a temperature measuring thermocouple, wherein the second material refers to a material different from the material used for forming the radio frequency electrode.

5. The radio frequency ablation device according to claim 4, wherein:
the second material is connected to the radio frequency electrode in any manner of welding, electroplating, sleeve joint, and pressure jointing.

6. The radio frequency ablation device according to claim 1, wherein:
multiple grooves are formed on the surface of the radio frequency ablation tube; and
the radio frequency ablation tube comprises a support tube configured at the central part of the ablation tube, and multiple wires configured on the outer surface of the support tube, wherein the multiple wires are configured around the circumferential direction of the support tube, and each of the wires extends along the length direction of the support tube; and a sealing layer for cladding the wire is configured outside each of the wires, and each neighboring sealing layers form a groove on the outer surface of the support tube.

7. The radio frequency ablation device according to claim 1, wherein:
one end of the tube body is used for being connected to the control handle, and the other end of the tube body is used for manufacturing an electrode section.

8. The radio frequency ablation device according to claim 7, wherein:
the shape of the electrode material is annular, and the electrode material is sleeved on the wound metal wire.

9. The radio frequency ablation device according to claim 1, wherein:
the temperature-controlling radio frequency instrument comprises a central processing and control module; a radio frequency releasing module, a impedance measuring module, a temperature monitoring module, and an alarm and automatic storage module that separately connected to the central processing and control module.

* * * * *